United States Patent [19]

Shida et al.

[11] Patent Number: 5,162,583

[45] Date of Patent: Nov. 10, 1992

[54] BENZYLETHER DERIVATIVES

[75] Inventors: Takafumi Shida; Hideo Arabori; Takeo Watanabe; Yoshikazu Kubota; Isao Ichinose; Yoichi Kanda; Shiro Yamazaki; Hiroyasu Shinkawa, all of Iwaki, Japan

[73] Assignee: Kureha Kagaku Kogyo Kabushiki Kaisha, Tokyo, Japan

[21] Appl. No.: 588,996

[22] Filed: Sep. 27, 1990

Related U.S. Application Data

[62] Division of Ser. No. 162,699, Mar. 1, 1988, Pat. No. 4,973,353.

[30] Foreign Application Priority Data

Mar. 10, 1987 [JP] Japan ............................ 62-54579
Jun. 19, 1987 [JP] Japan ........................... 62-153031

[51] Int. Cl.$^5$ ............................................ C07C 211/29
[52] U.S. Cl. ...................................... 564/442; 71/92; 548/266.8; 564/443; 568/928; 568/937; 568/938; 568/939; 568/940
[58] Field of Search ............... 564/442, 443; 568/928, 568/937, 938, 939, 940

[56] References Cited

U.S. PATENT DOCUMENTS

| | | | |
|---|---|---|---|
| 3,520,930 | 7/1970 | Clark et al. | 564/443 |
| 4,101,582 | 7/1978 | Lutz et al. | 564/443 |
| 4,165,231 | 8/1979 | Lutz et al. | 71/121 |
| 4,395,577 | 7/1983 | Maulding | 71/121 |
| 4,492,597 | 1/1985 | Aoki et al. | 71/92 |
| 4,795,484 | 1/1989 | Aoki et al. | 71/92 |
| 4,820,334 | 4/1989 | Shida et al. | 71/92 |
| 4,829,058 | 5/1989 | Seydel et al. | 514/155 |
| 4,846,882 | 7/1989 | Chang | 71/96 |
| 4,973,353 | 11/1990 | Shida et al. | 548/266.8 |
| 4,983,209 | 1/1991 | Shida et al. | 348/266.8 |

FOREIGN PATENT DOCUMENTS

| | | |
|---|---|---|
| 2412119 | 9/1974 | Fed. Rep. of Germany ...... 564/442 |
| 61-289066 | 12/1986 | Japan . |
| WO87/04049 | 7/1987 | PCT Int'l Appl. . |
| 2120665B | 12/1983 | United Kingdom . |

OTHER PUBLICATIONS

*Chemical Abstracts*, vol. 100, No. 19, column 1, Abstract No. 156607x Mar., 1982.
STN International ACS No. 69885-62-7, p. 220, Mar. 27, 1992.
STN International, ACS No. 69885-39-8, p. 228, Mar. 27, 1992.
ACS No. 10342-71-9, 1992.
Ishikawa, N. et al, "Preparation and properties of heptafluoroisopropyl benzoate, etc." CA 83, 113428c, 1975.
Shida, T. et al, "Preparation of 1,5-diphenyl-1H-1,2-,4-triazole-3-carboxamides, etc.", CA 110, 95247n, 1989.
Shida, T., et al, "Preparation and Testing of 1,5--draryl-4,5-dihydro, etc", CA 110, 57672g, 1989.
Shida, T., et al, "Benzyl ethers useful as intermediates for 1,2,4-triazole, etc", CA 109, 210680s, 1988.

*Primary Examiner*—Richard L. Raymond
*Assistant Examiner*—Brian M. Burn
*Attorney, Agent, or Firm*—Nixon & Vanderhye

[57] ABSTRACT

Disclosed herein are the derivative of benzyl ether represented by the formula (I)

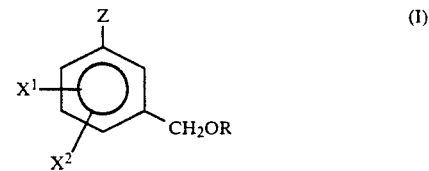

which is useful as an intermediate compound of the derivatives of 1,5-diphenyl-1H-1,2,4- triazole-3-carboxamide represented by the formula (II),

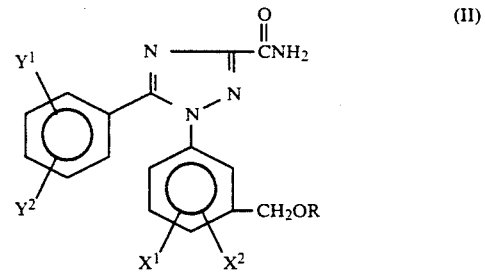

wherein R is a straight-chain alkyl group having 1 to 10 carbon atoms which is non-substituted or substituted with 1 to 19 fluorine atoms, a branched alkyl group having 3 to 10 carbon atoms which is non-substituted or substituted with 1 to 19 fluorine atoms, a cyclic alkyl group having 3 to 10 carbon atoms, an alkyl group having 1 to 3 carbon atoms which is substituted with an alicyclic structure having 3 to 7 carbon atoms, a phenyl group or an aralkyl group having 7 to 9 carbon atoms; $X^1$ is a halogen or an alkyl group having 1 to 3 carbon atoms; $X^2$ is a hydrogen, a halogen or an alkyl group having 1 to 3 carbon atoms; $Y^1$ is a hydrogen or a fluorine; $Y^2$ is a hydrogen or a fluorine; and Z is a nitro group or an amino group.

15 Claims, No Drawings

BENZYLETHER DERIVATIVES

CROSS-REFERENCE TO RELATED APPLICATION

The present invention is a continuation-in-part application of U.S. patent application Ser. No. 162,699 filed on Mar. 1, 1988, now U.S. Pat. No. 4,973,353.

BACKGROUND OF THE INVENTION

The present invention relates to the derivative of benzyl ether represented by the formula (I):

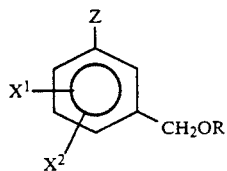
(I)

as an intermediate compound of the derivatives of 1,5-diphenyl-1H-1,2,4-triazole-3-carboxamide represented by the formula (II) having the excellent selective herbicidal activity.

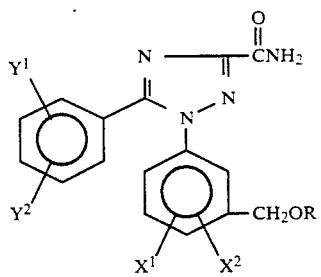
(II)

In formula (I) and formula (II), R is a straight-chain alkyl group having 1 to 10 carbon atoms which is non-substituted or substituted with 1 to 19 fluorine atoms, a branched alkyl group having 3 to 10 carbon atoms which is non-substituted or substituted with 1 to 19 fluorine atoms, a cyclic alkyl group having 3 to 10 carbon atoms, an alkyl group having 1 to 3 carbon atoms which is substituted with an alicyclic structure having 3 to 7 carbon atoms, a phenyl group or an aralkyl group having 7 to 9 carbon atoms; $X^1$ is a halogen or an alkyl group having 1 to 3 carbon atoms; $X^2$ is a hydrogen, a halogen or an alkyl group having 1 to 3 carbon atoms; $Y^1$ is a hydrogen or a fluorine; $Y^2$ is a hydrogen or a fluorine; and Z is a nitro group or an amino group.

Rice, wheat and corn are the important farm products, and use of herbicides is essential for protecting these crops from harm by weeds so as to attain an increased yield.

It is known that the derivatives of 1,5-diphenyl-1H-1,2,4-triazole-3-carboxamide have a herbicidal activity. For instance, Japanese Patent Application Kokai (Laid-Open) No. 193406/82 discloses a herbicidal composition containing as its active ingredient a derivative of 1,2,4-triazole represented by the formula:

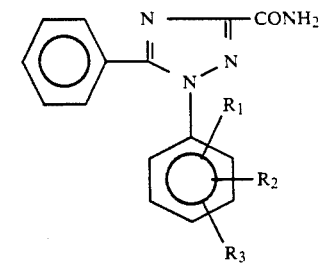

wherein $R_1$ is a hydrogen atom, a fluorine atom, a chlorine atom, an iodine atom, a lower alkyl group having 1 to 3 carbon atoms, an alkyl group substituted with fluorine, a nitro group or a methoxy group; $R_2$ is a hydrogen atom, a chlorine atom or a methyl group; and $R_3$ is a hydrogen atom or a methyl group.

Also, in Japanese Patent Application Kokai (Laid-Open) No. 98004/84 is disclosed a herbicidal composition containing a derivative of 1,2,4-triazole represented by the formula:

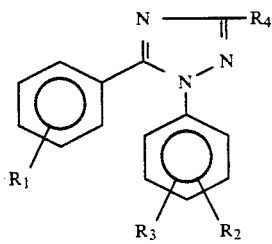

wherein $R_1$ and $R_2$ represent independently a hydrogen atom, a halogen atom, an alkyl group or a halogenoalkyl group; $R_3$ is a hydrogen atom, a halogen atom or an alkyl group; and $R_4$ is a cyano, carbamoyl, thiocarbamoyl, N-alkylcarbamoyl, N-halogenoalkylcarbamoyl, N-methoxyalkylcarbamoyl, N-alkenylcarbamoyl, N-halogenoalkenylcarbamoyl, N-acylcarbamoyl, N-halogenoacylcarbamoyl or N-methylthiocarbamoyl group.

These derivatives, however, are still unsatisfactory in herbicidal activity and selectivity. Therefore, development of the compounds having high herbicidal activities and excellent selectivity enabling killing of weeds alone without doing any harm to the crops such as rice, wheat, corn, etc., has been strongly desired.

On the other hand, a derivative of benzyl ether represented by the formula:

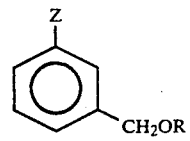

wherein R represents a straight chain alkyl group having 1 to 7 carbon atoms, isopropyl group, phenyl group, benzyl group, propynyl group and 2,2,2-trifluoroethyl group are known.

For example, these compounds are described in The Journal of the Chemical Society", Vol. 1954 (1954) Page 4127, Chekoslovenska Farmacie, Vol. 30 (1981) Page 184, U.S. Pat. No. 4,348,223 (1982), Journal of Pharmaceutical Sciences Vol. 56 (1976) Page 871, Chemical Abstracts, Vol 83 No. 92303 and Analytical Chemistry, Vol. 54 (1982) Page 529.

As a result of the present inventor's studies for providing a compound showing a high herbicidal activity but being practically harmless to such crops as rice, wheat and corn, it has been found that the derivative of benzyl ether represented by the formula (I) is useful as an intermediate compound of the derivatives of 1,5-diphenyl-1H-1,2,4-triazole-3-carboxy amide represented by the formula (II) having excellent selective herbicidal activities against grass weeds and, in particular, broadleaf weeds while doing no harm to such crops as rice, wheat and corn.

SUMMARY OF THE INVENTION

The object of the present invention is to provide the derivative of benzyl ether which is represented by the following formula (I)

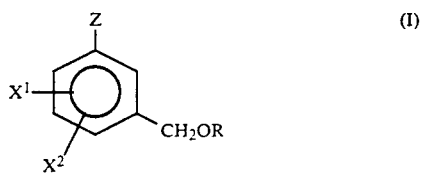

wherein R is a straight-chain alkyl group having 1 to 10 carbon atoms which is non-substituted or substituted with 1 to 19 fluorine atoms, a branched alkyl group having 3 to 10 carbon atoms which is non-substituted or substituted with 1 to 19 fluorine atoms, a cyclic alkyl group having 3 to 10 carbon atoms, an alkyl group having 1 to 3 carbon atoms which is substituted with an alicyclic structure having 3 to 7 carbon atoms, a phenyl group or an aralkyl group having 7 to 9 carbon atoms; $X^1$ is a halogen or an alkyl group having 1 to 3 carbon atoms; $X^2$ is a hydrogen, a halogen or an alkyl group having 1 to 3 carbon atoms; Z is a nitro group or an amino group; and which is useful as an intermediate compound of the derivatives of 1,5-diphenyl 1H-1,2,4-triazole-3-carboxamide represented by the formula (II) having the excellent selective herbicidal activity;

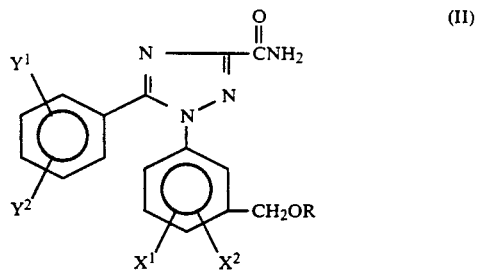

wherein R is a straight-chain alkyl group having 1 to 10 carbon atoms which is non-substituted or substituted with 1 to 19 fluorine atoms, a branched alkyl group having 3 to 10 carbon atoms which is non-substituted or substituted with 1 to 19 fluorine atoms, a cyclic alkyl group having 3 to 10 carbon atoms, an alkyl group having 1 to 3 carbon atoms which is substituted with an alicyclic structure having 3 to 7 carbon atoms, a phenyl group or an aralkyl group having 7 to 9 carbon atoms; $X^1$ is a halogen or an alkyl group having 1 to 3 carbon atoms; $X^2$ is a hydrogen, a halogen or an alkyl group having 1 to 3 carbon atoms; $Y^1$ is a hydrogen or a fluorine; and $Y^2$ is a hydrogen or a fluorine.

DETAILED DESCRIPTION

The derivative of benzyl ether according to the present invention is a compound represented by the general formula (I):

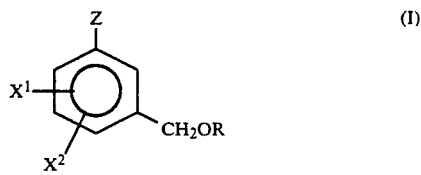

wherein R is a straight-chain alkyl group having 1 to 10 carbon atoms which is non-substituted or substituted with 1 to 19 fluorine atoms, a branched alkyl group having 3 to 10 carbon atoms which is non-substituted or substituted with 1 to 19 fluorine atoms, a cyclic alkyl group having 3 to 10 carbon atoms, an alkyl group having 1 to 3 carbon atoms which is substituted with an alicyclic structure having 3 to 7 carbon atoms, a phenyl group or an aralkyl group having 7 to 9 carbon atoms; $X^1$ is a halogen or an alkyl group having 1 to 3 carbon atoms; $X^2$ is a hydrogen, a halogen or an alkyl group having 1 to 3 carbon atoms; and Z is a nitro group or an amino group.

When Z is a nitro group, formula (I) is nitrobenzyl ether represented by formula (III),

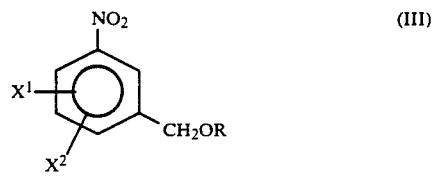

and
when Z is an amino group, formula (I) is the derivative of aniline represented by formula (IV).

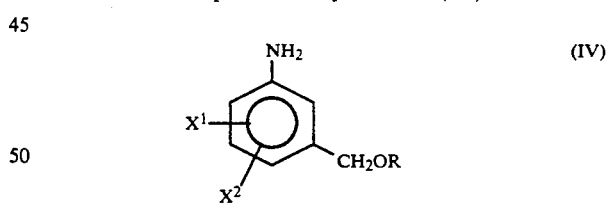

In formula (III) and (IV), R, $X^1$, $X^2$ are as defined above.

A preferred compound represented by the general formula (I) is a compound in which R is a straight-chain alkyl group having 3 to 6 carbon atoms which is non-substituted or substituted with 3 to 12 fluorine atoms, a branched alkyl group having 4 to 7 carbon atoms which is non-substituted or substituted with 3 to 12 fluorine atoms, a cyclic alkyl group having 4 to 7 carbon atoms, an alkyl group having 1 to 3 carbon atoms which is substituted with an alicyclic structure having 3 to 7 carbon atoms, a phenyl group or an aralkyl group having 7 to 9 carbon atoms;

$X^1$ is a halogen or an alkyl group having 1 to 3 carbon atoms; $X^2$ is a hydrogen, a halogen or an alkyl group having 1 to 3 carbon atoms; and Z represents a nitro group or an amino group.

A further preferred compound represented by the general formula (I) is a compound in which R is a straight-chain alkyl group having 2 to 4 carbon atoms which is substituted with 3 to 7 fluorine atoms, $X^1$ is a chlorine or a methyl group, $X^2$ is a hydrogen; and Z represents a nitro group or an amino group.

More specifically, a preferred compound is exemplified by the following compounds:

4-chloro-3-(2,2,2-trifluoroethoxy)methyl-1-nitrobenzene.
4-chloro-3-(2,2,4,4-tetrafluoropropoxy)methyl-1-nitrobenzene.
4-chloro-3-(2,2,3,3,3-pentafluoropropoxy)methyl-1-nitrobenzene.
4-chloro-3-(2,2,3,4,4,4-hexafluorobutoxy)methyl-1-nitrobenzene.
4-chloro-3-(2,2,3,3,4,4,4-heptafluorobutoxy)methyl-1-nitrobenzene.
3-(2,2,3,3,3-pentafluoropropoxy)methyl-4-methyl-1-nitrobenzene.
4-chloro-3-(2,2,2-trifluoroethoxy)methyl-aniline.
4-chloro-3-(2,2,4,4-tetrafluoropropoxy)methyl-aniline.
4-chloro-3-(2,2,3,3,3-pentafluoropropoxy)methyl-aniline.
4-chloro-3-(2,2,3,4,4,4-hexafluorobutoxy)methyl-aniline.
4-chloro-3-(2,2,3,3,4,4,4-heptafluorobutoxy)methylaniline.
3-(2,2,3,3,3-pentafluoropropoxy)methyl-4-methylaniline.

The derivative of benzyl ether represented by the formula (I) according to the present invention is useful as an intermediate compound of the derivatives of 1,5-diphenyl-1H-1,2,4-triazole-3-carboxyamide represented by the formula (II) having the excellent selective herbicidal activity.

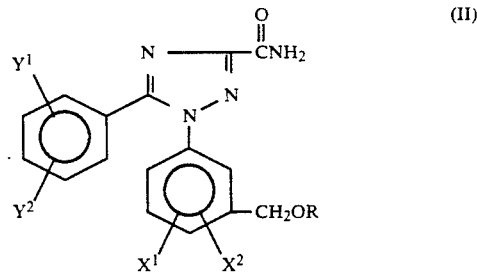

wherein R, $X^1$, $X^2$ are as defined above and $Y^1$ is a hydrogen or a fluorine; and $Y^2$ is a hydrogen or a fluorine.

Illustrative examples of the compounds of formula (II) and their physicochemical properties are shown in Table 1. The results of elemental analysis of these compounds are shown in Table 2.

TABLE 1

| No. | R | $X^1$ | $X^2$ | $Y^1$ | $Y^2$ | Yield of synthesis (%) | Melting point (°C.) | NMR spectrum (CDCl$_3$, δ, ppm, 60 MHz) |
|---|---|---|---|---|---|---|---|---|
| 1 | —CH$_2$CH$_3$ | 4-Cl | H | H | H | 77.5 | 127~129 | 1.13(3H, t, 7Hz), 3.47(2H, q, 7Hz), 4.56(2H, s), 6.6~7.6(10H, m) |
| 2 | —(CH$_2$)$_3$CH$_3$ | 4-Cl | H | H | H | 94.2 | 96~98 | 1.00(3H, t, 6Hz), 1.13~1.85(4H, m), 3.46(2H, t, 6Hz), 4.52(2H, s), 6.9~7.9(10H, m) |
| 3 | —(CH$_2$)$_4$CH$_3$ | 4-Cl | H | H | H | 84.6 | 133~135 | 0.85(3H, t, 6Hz), 1.05~1.73(6H, m), 3.30(2H, t, 6Hz), 4.43(2H, s), 6.3(1H, bs), 6.8~7.5(9H, m) |
| 4 | —(CH$_2$)$_2$CH(CH$_3$)$_2$ | 4-Cl | H | H | H | 95.7 | 121~123 | 0.87(6H, d, 6Hz), 1.20~2.00(3H, m), 3.50(2H, t, 6Hz), 4.53(2H, s), 6.68(1H, bs), 7.20(1H, bs), 7.3~7.8(8H, m) |
| 5 | —CH$_2$—C(CH$_3$)$_3$ | 4-Cl | H | H | H | 89.0 | 115~118 | 0.81(9H, s), 3.05(2H, s), 4.50(2H, s), 6.3(1H, bs), 6.9~7.6(9H, m) |
| 6 | —(CH$_2$)$_5$CH$_3$ | 4-Cl | H | H | H | 87.2 | 118~119 | 0.87(3H, t, 6Hz), 1.0~2.1(8H, m), 3.41(2H, t, 6Hz), 4.53(2H, s), 2.6(1H, bs), 7.0~7.8(9H, m) |
| 7 | —(CH$_2$)$_7$CH$_3$ | 4-Cl | H | H | H | 74.5 | 104~107 | 0.86(3H, m), 1.06~1.66(12H, m), 3.41(2H, t, 6Hz), 4.50(2H, s), 6.35(1H, bs), 7.0~7.6(9H, m) |
| 8 | —CH$_2$—cyclohexyl | 4-Cl | H | H | H | 82.5 | 138~140 | 0.6~1.9(11H, m), 3.19(2H, d, 6Hz), 4.47(2H, s), 6.6~7.9(10H, m) |
| 9 | —phenyl | 4-Cl | H | H | H | 77.3 | 164~166 | 5.10(2H, s), 6.2(1H, bs), 6.7~7.7(14H, m) |

TABLE 1-continued

| No. | R | X¹ | X² | Y¹ | Y² | Yield of synthesis (%) | Melting point (°C.) | NMR spectrum (CDCl₃, δ, ppm. 60 MHz) |
|---|---|---|---|---|---|---|---|---|
| 10 | —CH₂—C₆H₅ | 4-Cl | H | H | H | 85.0 | 96~98 | 4.50(2H, s), 4.56(2H, s), 6.6~7.7(15H, m) |
| 11 | —CH₂CF₃ | 4-Cl | H | H | H | 78.0 | 114~116 | 3.88(2H, q, 9Hz), 4.80(2H, s), 7.0~7.8(10H, m) |
| 12 | —CH₂CF₂CHF₂ | 4-Cl | H | H | H | 93.3 | 117~119 | 3.78(2H, tt, 13, 2Hz), 4.66(2H, s), 5.76(1H, tt, 54, 5Hz), 7.3~7.8(10H, m) |
| 13 | —CH₂CF₂CF₃ | 4-Cl | H | H | H | 80.8 | 138~140 | 3.78(2H, tq, 13, 2Hz), 4.73(2H, s), 6.6~7.8(10H, m) |
| 14 | —CH₂CF₂CHFCF₃ | 4-Cl | H | H | H | 92.5 | 94~96 | 3.20~4.13(2H, m), 4.75(2H, s), 5.32(1H, d, 6-plet, 50, 6Hz), 6.82(1H, bs), 7.30(1H, bs), 7.4~7.8(8H, m) |
| 15 | —CH₂(CF₂)₂CF₃ | 4-Cl | H | H | H | 87.2 | 135~136 | 3.97(2H, tt, 13.5, 2H), 4.74(2H, s), 6.6~7.8(10H, m) |
| 16 | —CH₂CF₂CF₃ | 4-Br | H | H | H | 72.7 | 141~143 | 3.88(2H, tq, 13, 1Hz), 4.67(2H, s), 6.7~7.9(10H, m) |
| 17 | —(CH₂)₂CH(CH₃)₂ | 4-Br | H | H | H | 89.4 | 128~130 | 0.85(6H, d, 6Hz), 1.1~2.1(3H, m), 3.47(2H, t, 6Hz), 4.46(2H, s), 6.8~7.9(10H, m) |
| 18 | —CH₂CF₂CF₃ | 4-I | H | H | H | 83.5 | 83~85 | 3.86(2H, tq, 13, 2Hz), 4.56(2H, s), 6.3(1H, bs), 7.06(1H, dd, 8, 3Hz), 7.2~7.6(7H, m), 7.85(1H, d, 8Hz) |
| 19 | —CH₂CF₂CF₃ | 4-Cl | 6-Cl | H | H | 82.1 | 187~189 | 3.94(2H, tq, 13, 2Hz), 4.70(2H, s), 6.3~7.7(9H, m) |
| 20 | —(CH₂)₂CH(CH₃)₂ | 4-Cl | 6-Cl | H | H | 91.4 | 126~128 | 0.87(6H, d, 6Hz), 1.2~1.9(3H, m), 3.52(2H, t, 6Hz), 4.53(2H, s), 6.9~7.9(8H, m), 6.2(1H, bs) |
| 21 | —CH₂CF₂CF₃ | 2-Cl | H | H | H | 89.7 | 113~115 | 3.96(2H, tq, 13, 2Hz), 4.70(2H, s), 7.2~7.7(10H, m)* |
| 22 | —CH₂CF₂CF₃ | 6-Cl | H | H | H | 74.5 | 213~215 | 3.97(2H, tq, 13, 2Hz), 4.73(2H, s), 6.1~7.8(10H, m) |
| 23 | —(CH₂)₂CH(CH₃)₂ | 4-Cl | H | 2-F | H | 82.3 | 113~115 | 0.87(6H, d, 6Hz), 1.1~2.1(3H, m), 3.40(2H, t, 6Hz), 4.47(2H, s), 6.5~7.9(9H, m) |
| 24 | —CH₂CF₂CF₃ | 4-Cl | H | 2-F | H | 62.8 | 104~106 | 3.87(2H, tq, 12, 1Hz), 4.67(2H, s), 6.7~7.8(9H, m) |
| 25 | —(CH₂)₂CH(CH₃)₂ | 4-Cl | H | 2-F | 4-F | 96.7 | 84~86 | 0.87(6H, d, 6Hz), 1.2~2.0(3H, m), 3.43(2H, t, 6Hz), 4.47(2H, s), 6.4(1H, bs), 6.6~7.8(7H, m) |
| 26 | —(CH₂)₂CH(CH₃)₂ | 4-Cl | H | 2-F | 6-F | 87.5 | 88~90 | 0.90(6H, d, 6Hz), 1.2~2.0(3H, m), 3.43(2H, t, 6Hz), 4.47(2H, s), 6.3(1H, bs), 6.8~7.6(7H, m) |
| 27 | —(CH₂)₂CH(CH₃)₂ | 4-CH₃ | H | H | H | 90.0 | 83~85 | 0.87(6H, d, 6Hz), 1.45(2H, q, 6.6Hz), 1.66(1H, m), 2.36(3H, s), 3.44(2H, t, 6.6Hz), 4.44(2H, s), 5.74(1H, bs), 7.09(1H, bs), 7.15~7.60(8H, m)** |
| 28 | —CH₂CF₂CF₃ | 4-CH₃ | H | H | H | 95.5 | 127~129 | 2.37(3H, s), 3.80(2H, tq, 13, 2, 1.0Hz), 4.62(2H, s), 5.76(1H, bs), 7.10(1H, bs), 7.2~7.6(8H, m)** |
| 29 | —CH₂CH(CH₃)CH₂CH₃ | 4-Cl | H | H | H | 66.3 | 142~143 | 0.85(3H, t, 6Hz), 0.84(3H, d, 6Hz), 1.0~2.25(3H, m), 3.31(2H, d, 6Hz), 4.58(2H, s), 6.5(1H, bs), 7.0~7.73(9H, m) |
| 30 | —(CH₂)₃CH₃ | 4-Br | H | H | H | 65.3 | 105~106 | 0.97(3H, t, 6Hz), 1.0~1.7(4H, m), 3.39(2H, t, 6Hz), 4.42(2H, s), 6.4~ |

TABLE 1-continued

| No. | R | X¹ | X² | Y¹ | Y² | Yield of synthesis (%) | Melting point (°C.) | NMR spectrum (CDCl₃. δ, ppm. 60 MHz) |
|---|---|---|---|---|---|---|---|---|
| | | | | | | | | 7.6(10H, m) |
| 31 | —(CH₂)₃CH₃ | 4-Br | H | 2-F | H | 70.2 | 126~128 | 0.88(3H, t, 6Hz), 1.0~1.8(4H, m), 3.37(2H, t, 6Hz), 4.37(2H, s), 6.3~7.8(9H, m) |
| 32 | —CH₂CF₂CF₃ | 4-Cl | 6-F | H | H | 58.8 | 177~179 | 3.96(2H, tq, 13, 2Hz), 4.73(2H, s), 6.21(1H, bs), 6.9~7.6(6H, m), 7.25(1H, d, 10Hz), 7.68(1H, d, 8Hz) |
| 33 | —CH₂CF₃ | 4-Br | H | H | H | 52.8 | 120~122 | 3.77(2H, q, 9Hz), 4.67(2H, s), 6.1~7.7(10H, m) |
| 34 | —(CH₂)₃CH₃ | 4-Cl | H | 2-F | H | 90.4 | 95~97 | 0.85(3H, t, 6Hz), 1.0~1.8(4H, m), 3.32(2H, t, 6Hz), 4.40(2H, s), 6.5~7.7(9H, m) |
| 35 | —CH₂CF₂CF₃ | 4-F | H | H | H | 83.6 | 141~142 | 3.85(2H, tq, 14, 2Hz), 4.65(2H, s), 6.4~7.7(10H, m) |
| 36 | —(CH₂)₃CH₃ | 4-CH₃ | H | H | H | 59.8 | 101~103 | 0.89(3H, t, 7.3Hz), 1.32(2H, 6-plet, 7.3Hz), 1.53(2H, 5-plet, 7.3Hz), 2.36(3H, s), 3.41(2H, t, 7.3Hz), 4.45(2H, s), 7.15~7.6(8H, m), 5.8(1H, bs), 7.09(1H, bs)** |
| 37 | 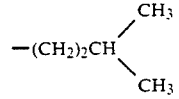 —(CH₂)₂CH(CH₃)CH₃ | 4-CH₃ | H | 2-F | 6-F | 85.3 | Amorphous | 0.87(6H, d, 6.4Hz), 1.44(2H, q, 6.4Hz), 1.66(1H, 9-plet, 6.4Hz), 2.30(3H, s), 3.40(2H, t, 6.4Hz), 4.39(2H, s), 6.96(2H, t, 8.3Hz), 7.13(1H, d, 7.8Hz), 7.18(1H, dd, 7.8, 1.5Hz), 7.37(1H, d, 1.5Hz), 7.38~7.52(1H, m), 5.87(1H, bs), 7.10(1H)** |
| 38 | 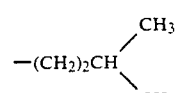 —(CH₂)₂CH(CH₃)CH₃ | 4-CH₃ | H | 2-F | H | 58.5 | 94~96 | 0.87(6H, d, 6.8Hz), 1.42(2H, q, 6.8Hz), 1.64(1H, 9-plet, 6.8Hz), 2.31(3H, s), 3.39(2H, t, 6.8Hz), 4.40(2H, s), 7.03(1H, t, 9.3Hz), 7.12~7.40(4H, m), 7.48(1H, m), 7.59(1H, td, 7.3, 2.0Hz), 5.83(1H, bs), 7.10(1H)** |
| 39 | —CH₂CF₂CHF₂ | 4-CH₃ | H | H | H | 77.0 | 118~120 | 2.33(3H, d), 3.70(2H, tt, 13, 2Hz), 4.53(2H, s), 5.76(1H, tt, 53, 5Hz), 6.5(1H, bs), 7.0~7.7(9H, m) |
| 40 | —CH₂CF₂CF₃ | 4-CH₃ | H | 2-F | H | 60.3 | 110~111 | 2.33(3H, s), 3.76(2H, t, 13.2Hz), 4.58(2H, s), 7.04(1H, t, 9.3Hz), 7.15~7.35(4H, m), 7.4~7.55(1H, m), 7.61(1H, td, 7.3, 2.0Hz(, 5.79(1H, bs), 7.10(1H, bs)** |
| 41 | —CH₂CF₂CF₃ | 4-CH₃ | H | 2-F | 6-F | 97.3 | 111~114 | 2.32(3H, s), 3.79(2H, t, 13.2Hz), 4.58(2h, s), 6.97(2H, t, 8.3Hz), 7.20(1H, d, 7.8Hz), 7.27(1H, dd, 7.8, 2.0Hz), 7.32(1H, d, 2.0Hz), 7.47(1H, m), 5.80(1H, bs), 7.10(1H, bs)** |
| 42 | —CH₂CF₂CHFCF₃ | 4-CH₃ | H | H | H | 68.5 | 114~115 | 2.30(3H, s), 3.36~3.96(2H, m), 4.48(2H, s), 4.96(H, d, 6-plet, 43, 6Hz), 6.1(1H, bs), 6.8~7.5(9H, m) |
| 43 | —CH₂(CF₂)₂CF₃ | 4-CH₃ | H | H | H | 82.1 | 116~118 | 2.35(3H, s), 3.68(2H, tq, 14, 2Hz), 4.60(2H, s), 6.9~7.7(10H, m) |
| 44 | —(CH₂)₂CH₃ | 4-CH₃ | H | H | H | 84.5 | 84~86 | 0.85(3H, t, 6Hz), 1.53(2H, 6-plet, 6Hz), 2.30(3H, s), 3.28(2H, t, 6Hz), 4.35(2H, s), 6.6~7.6(10H, m) |
| 45 | —(CH₂)₅CH₃ | 4-CH₃ | H | H | H | 62.3 | 78~80 | 0.87(3H, t, 6Hz), 1.0~1.9(8H, m), 2.33(3H, s), 3.35(2H, t, 6Hz), 4.45(2H, s), 6.4~7.6(10H, m) |
| 46 | —CH₂CF₃ | 4-CH₃ | H | H | H | 75.6 | 145~146 | 2.33(3H, s), 3.69(2H, q, 8Hz), 4.57(2H, s), 6.7(1H, bs), 7.0-7.6(9H, m) |
| 47 | —CH₂(CF₂)₂CF₃ | 4-Br | H | H | H | 83.6 | 155~156 | 3.92(2H, tt, 14, 2Hz), 4.66(2H, s), 6.9(1H, bs), 7.0~7.6(9H, m) |
| 48 | —CH₂CF₂CF₃ | 4-CH₂CH₃ | H | H | H | 86.6 | 114~115 | 1.21(3H, t, 8Hz), 2.69(2H, q, 8Hz), 3.76(2H, tq, 13, 2Hz), 4.60(2H, s), |

TABLE 1-continued

| No. | Substituent in formula (I)*** | | | | | Yield of synthesis (%) | Melting point (°C.) | NMR spectrum (CDCl₃, δ, ppm, 60 MHz) |
|---|---|---|---|---|---|---|---|---|
| | R | X¹ | X² | Y¹ | Y² | | | |
| | | | | | | | | 6.7(1H, bs), 6.9~7.8(9H, m) |

*DHSO-d₆ was used as solvent.
**Measured at 250 MHz.
***The substituents were numbered as shown in the following formula.

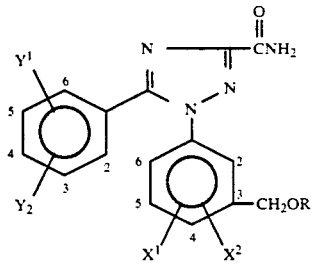

| TABLE 2 | | | | | | | | | | | | |
|---|---|---|---|---|---|---|---|---|---|---|---|---|
| | Calculated | | | Found | | | | | Calculated | | | Found | | |
| No. | C (%) | H (%) | N (%) | C (%) | H (%) | N (%) | No. | C (%) | H (%) | N (%) | C (%) | H (%) | N (%) |
| 1 | 60.59% | 4.80% | 15.70% | 60.76% | 4.97% | 15.87% | 35 | 51.36% | 3.18% | 12.61% | 51.38% | 3.30% | 12.76% |
| 2 | 62.42% | 5.50% | 14.56% | 62.52% | 5.60% | 14.66% | 36 | 69.21% | 6.64% | 15.37% | 69.40% | 6.78% | 15.29% |
| 3 | 63.23% | 5.81% | 14.05% | 63.30% | 5.87% | 14.11% | 37 | 63.76% | 5.84% | 13.52% | 63.69% | 5.74% | 13.56% |
| 4 | 63.23% | 5.81% | 14.05% | 63.35% | 5.93% | 14.16% | 38 | 66.65% | 6.36% | 14.13% | 66.81% | 6.55% | 14.11% |
| 5 | 63.23% | 5.81% | 14.05% | 63.40% | 5.97% | 14.21% | 39 | 56.87% | 4.30% | 13.26% | 56.91% | 4.12% | 13.46% |
| 6 | 63.99% | 6.10% | 13.57% | 64.01% | 6.12% | 13.59% | 40 | 52.41% | 3.52% | 12.22% | 52.23% | 3.71% | 12.11% |
| 7 | 65.37% | 6.63% | 12.70% | 65.30% | 6.56% | 12.63% | 41 | 50.43% | 3.17% | 11.76% | 50.04% | 3.29% | 11.84% |
| 8 | 65.01% | 5.93% | 13.18% | 64.83% | 5.75% | 13.01% | 42 | 53.39% | 3.84% | 11.86% | 53.35% | 4.04% | 11.66% |
| 9 | 65.27% | 4.23% | 13.84% | 65.15% | 4.12% | 13.72% | 43 | 51.44% | 3.49% | 11.43% | 51.24% | 3.63% | 11.57% |
| 10 | 65.95% | 4.57% | 13.37% | 65.80% | 4.42% | 13.22% | 44 | 68.55% | 6.33% | 15.99% | 68.74% | 6.48% | 15.86% |
| 11 | 52.63% | 3.44% | 13.64% | 52.48% | 3.28% | 13.49% | 45 | 70.38% | 7.19% | 14.27% | 70.43% | 7.06% | 14.35% |
| 12 | 51.54% | 3.41% | 13.64% | 52.48% | 3.28% | 13.49% | 46 | 58.46% | 4.39% | 14.35% | 58.56% | 4.35% | 14.17% |
| 13 | 49.53% | 3.06% | 12.16% | 49.33% | 2.87% | 11.97% | 46 | 43.26% | 2.54% | 10.09% | 43.07% | 2.65% | 10.23% |
| 14 | 48.75% | 3.07% | 11.37% | 48.74% | 3.06% | 11.36% | 48 | 55.51% | 4.21% | 12.33% | 55.32% | 4.32% | 12.53% |
| 15 | 47.03% | 2.76% | 10.97% | 47.23% | 2.96% | 11.17% | | | | | | | |
| 16 | 45.17% | 2.79% | 11.09% | 45.05% | 2.68% | 10.97% | | | | | | | |
| 17 | 56.89% | 5.23% | 12.64% | 57.06% | 5.40% | 12.80% | | | | | | | |
| 18 | 41.33% | 2.56% | 10.15% | 41.16% | 2.39% | 9.98% | | | | | | | |
| 19 | 46.08% | 2.65% | 11.31% | 46.2% | 2.83% | 11.50% | | | | | | | |
| 20 | 58.21% | 5.12% | 12.93% | 58.15% | 5.06% | 12.87% | | | | | | | |
| 21 | 49.53% | 3.06% | 12.16% | 49.33% | 2.87% | 11.97% | | | | | | | |
| 22 | 49.53% | 3.06% | 12.16% | 49.63% | 3.17% | 12.26% | | | | | | | |
| 23 | 60.50% | 5.32% | 13.44% | 60.31% | 5.12% | 13.24% | | | | | | | |
| 24 | 47.67% | 2.74% | 11.70% | 47.70% | 2.77% | 11.74% | | | | | | | |
| 25 | 58.00% | 4.87% | 12.88% | 58.03% | 4.89% | 12.91% | | | | | | | |
| 26 | 58.00% | 4.87% | 12.88% | 58.05% | 4.91% | 12.93% | | | | | | | |
| 27 | 69.82% | 6.92% | 14.80% | 69.95% | 7.05% | 14.93% | | | | | | | |
| 28 | 54.55% | 3.89% | 12.72% | 54.39% | 3.37% | 12.56% | | | | | | | |
| 29 | 63.23% | 5.81% | 14.05% | 63.50% | 6.02% | 14.16% | | | | | | | |
| 30 | 55.95% | 4.93% | 13.05% | 56.08% | 4.74% | 13.00% | | | | | | | |
| 31 | 53.70% | 4.51% | 12.53% | 53.63% | 4.7% | 12.38% | | | | | | | |
| 32 | 47.66% | 2.74% | 11.70% | 47.47% | 2.54% | 11.90% | | | | | | | |
| 33 | 47.49% | 3.10% | 12.31% | 47.67% | 2.95% | 12.49% | | | | | | | |
| 34 | 59.63% | 5.00% | 13.91% | 59.44% | 4.92% | 14.11% | | | | | | | |

The physicochemical properties of the formula (I) according to the present invention are shown in Table 3 and Table 4. By the way, these intermediates are the novel compounds.

Table 3 shows the physicochemical properties of the derivative of nitrobenzyl ether (III).

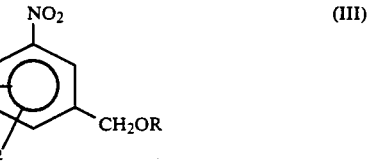

(III)

wherein, R, X¹ and X² are as defined in formula (I).

TABLE 3

| No. | Substituent in formula (III) | | | Yield of synthesis (%) | Boiling point °C./mmHg | IR (KBr, neat, cm⁻¹) | NMR (CDCl₃, δ, ppm, 60 MHz) |
|---|---|---|---|---|---|---|---|
| | X¹ | X² | R | | | | |
| 1 | 4-Cl | H | CH₂CH₃ | | | | |
| 2 | 4-Cl | H | (CH₂)₃CH₃ | | | | |
| 3 | 4-Cl | H | (CH₂)₄CH₃ | | | | |
| 4 | 4-Cl | H | (CH₂)₂CH(CH₃)CH₃ | 74.6 | 128.5/0.9 | 1530, 1350 | 0.93(6H, d, 6Hz), 1.4~2.1(3H, m), 3.60(2H, t, 6Hz), 4.57(1H, s), 7.47(1H, d, 9Hz), 8.07(1H, dd, 9, 3Hz), 8.37(1H, d, 3Hz) |
| 5 | 4-Cl | H | CH₂C(CH₃)₃ | | | | |

TABLE 3-continued

| No. | Substituent in formula (III) X¹ | X² | R | Yield of synthesis (%) | Boiling point °C./mmHg | IR (KBr, neat, cm$^{-1}$) | NMR (CDCl$_3$, δ, ppm, 60 MHz) |
|---|---|---|---|---|---|---|---|
| 6 | 4-Cl | H | (CH$_2$)$_5$CH$_3$ | | | | |
| 7 | 4-Cl | H | (CH$_2$)$_7$CH$_3$ | | | | |
| 8 | 4-Cl | H | —CH$_2$—cyclohexyl | | | | |
| 9 | 4-Cl | H | —phenyl | 45.9 | mp 84~85 | | 5.17(2H, s), 6.8~7.5(5H, m), 7.52(1H, d, 9Hz). 8.13(1H, dd, 3, 9Hz), 8.5(1H, d, 3Hz) |
| 10 | 4-Cl | H | —CH$_2$-phenyl | | | | |
| 11 | 4-Cl | H | CH$_2$CF$_3$ | 58.5 | Oil | 1540, 1350 | 4.05(2H, q, 9Hz), 4.83(2H, s). 7.53(1H, d, 8Hz). 8.12(1H, dd, 8, 3Hz), 8.35(1H, d, 3Hz) |
| 12 | 4-Cl | H | CH$_2$CF$_2$CHF$_2$ | | | | |
| 13 | 4-Cl | H | CH$_2$CF$_2$CF$_3$ | 68.8 | 125/0.3 | 1530, 1350 | 4.17(2H, tt, 13, 1Hz), 4.87(2H, s), 7.50(1H, d, 8Hz). 8.13(1H, dd, 8, 3Hz), 8.35(1H, d, 3Hz) |
| 14 | 4-Cl | H | CH$_2$CF$_2$CHFCF$_3$ | 89.5 | 123~125/0.2 | 1540, 1350 | 3.7~4.3(2H, m), 4.80(2H, s), 5.07(1H, d, 6-Plet, 49, 6Hz), 7.50(1H, d, 8Hz), 8.13(1H, dd, 8, 3Hz), 8.30(1Hz, d, 3Hz) |
| 15 | 4-Cl | H | CH$_2$(CF$_2$)$_2$CF$_3$ | 88.3 | Oil | 1550, 1360 | 4.83(2H, tt, 13, 2Hz), 4.85(2H, s). 7.55(1H, d, 8Hz), 8.15(1H, dd, 8, 3Hz), 8.40(1H, d, 3Hz) |
| 16 | 4-Br | H | CH$_2$CF$_2$CF$_3$ | | | | |
| 17 | 4-Br | H | (CH$_2$)$_2$CH(CH$_3$)$_2$ | | | | |
| 18 | 4-I | H | CH$_2$CF$_2$CF$_3$ | | | | |
| 19 | 4-Cl | 6-Cl | CH$_2$CF$_2$CF$_3$ | | | | |
| 20 | 4-Cl | 6-Cl | (CH$_2$)$_2$CH(CH$_3$)$_2$ | | | | |
| 21 | 2-Cl | H | CH$_2$CF$_2$CF$_3$ | | | | |
| 22 | 6-Cl | H | CH$_2$CF$_2$CF$_3$ | | | | |
| 23 | 4-CH$_3$ | H | (CH$_2$)$_2$CH(CH$_3$)$_2$ | 28.0 | 130~131/0.8 | 1515, 1345 | 0.92(6H, d, 6.6Hz), 1.55(2H, q, 6.6Hz), 1.75(1H, 9-plet, 6.6Hz), 2.40(3H, s), 3.57(2H, t, 6.6Hz), 4.52(2H, s), 7.30(1H, d, 8.3Hz), 8.05(1H, dd, 8.3, 2.4), 8.24(1H, d, 2.4Hz)* |
| 24 | 4-CH$_3$ | H | CH$_2$CF$_2$CF$_3$ | 95.5 | mp 53.5~54.5 | 1520, 1340 | 2.43(3H, s), 4.00(2H, t, 12.8Hz), 4.72(2H, s), 7.36(1H, d, 8.3Hz), 8.11(1H, dd, 8.3, 2.4Hz)* |
| 25 | 4-Cl | H | —CH$_2$CH(CH$_3$)CH$_2$CH$_3$ | | | | |
| 26 | 4-Br | H | (CH$_2$)$_3$CH$_3$ | | | | |
| 27 | 4-Cl | 6-F | CH$_2$CF$_2$CF$_3$ | | | | |
| 28 | 4-Br | H | CH$_2$CF$_3$ | | | | |
| 29 | 4-F | H | CH$_2$CF$_2$CF$_3$ | 41.0 | Oil | | 4.03(2H, tt, 13, 1Hz), 4.78(2H, s), |

TABLE 3-continued

| No. | Substituent in formula (III) X¹ | X² | R | Yield of synthesis (%) | Boiling point °C./mmHg | IR (KBr, neat, cm⁻¹) | NMR (CDCl₃, δ, ppm, 60 MHz) |
|---|---|---|---|---|---|---|---|
| 30 | 4-CH₃ | H | (CH₂)₃CH₃ | 71.3 | 88~89/0.02 | 1510, 1340 | 7.00~8.50(3H, m) 0.94(3H, t, 7.3Hz), 1.43(2H, 6-plet, 7.3Hz), 1.65(2H, m), 2.40(3H, s), 3.55(2H, t, 6.8Hz), 4.52(2H, s), 7.30(1H, d, 8.3Hz), 8.05(1H, dd, 8.3, 2.4Hz), 8.24(1H, d, 2.4Hz)* |
| 31 | 4-CH₃ | H | CH₂CF₂CHF₂ | | | | |
| 32 | 4-CH₃ | H | CH₂CF₂CHFCF₃ | 36.0 | 131~133.5/0.2 | 1520, 1345 | 2.43(3H, 2), 3.63~4.20(2H, m), 4.70(2H, s), 4.93(1H, 6-plet, 50.6Hz), 7.35(1H, d, 8Hz), 8.08(1H, dd, 8, 3Hz), 8.16(1H, d, 3Hz) |
| 33 | 4-CH₃ | H | CH₂(CF₂)₂CF₃ | 48.8 | 121~122/0.2 | 1517, 1340 | 2.36(3H, s), 3.98(2H, tq, 13, 2Hz), 4.65(2H, s), 7.18(1H, d, 8Hz), 7.90(1H, dd, 8, 3Hz), 8.06(1H, d, 3Hz) |
| 34 | 4-CH₃ | H | (CH₂)₂CH₃ | | | | |
| 35 | 4-CH₃ | H | (CH₂)₅CH₃ | | | | |
| 36 | 4-CH₃ | H | CH₂CF₃ | | | | |
| 37 | 4-Br | H | CH₂(CF₂)₂CF₃ | | | | |
| 38 | 4-CH₂CH₃ | H | CH₂CF₂CF₃ | | | | |

*Measured at 250 MHz.

Table 4 shows the physicochemical properties of the derivative of aniline (IV).

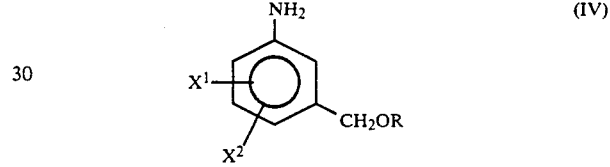

(IV)

wherein, R, X¹ and X² are as defined in formula (I).

TABLE 4

| No. | Substituent in formula (IV) X¹ | X² | R | Yield of synthesis (%) | Boiling point °C./mmHg | IR (KBr, neat, cm⁻¹) | NMR (CDCl₃, δ, ppm, 60 MHz) |
|---|---|---|---|---|---|---|---|
| 1 | 4-Cl | H | CH₂CH₃ | | | | |
| 2 | 4-Cl | H | (CH₂)₃CH₃ | | | | |
| 3 | 4-Cl | H | (CH₂)₄CH₃ | 79.0 | | 3460, 3360, 2960, 2940, 2860 | 0.86(3H, t, 5Hz), 1.06~2.00(6H, m), 3.47(2H, t, 5Hz), 3.56(2H, s), 4.45(2H, s), 6.38(1H, dd, 8, 3Hz), 6.71(1H, d, 3Hz), 6.98(1H, d, 8Hz) |
| 4 | 4-Cl | H | (CH₂)₂CH(CH₃)CH₃ | 45.0 | 126/0.9 | 3460, 3360, 3230 | 0.90(6H, d, 6Hz), 1.2~2.1(3H, m), 3.50(2H, t, 6Hz), 3.63(2H, s), 4.43(2H, s), 6.37(1H, dd, 8, 3Hz), 6.72(1H, d, 3Hz), 7.00(1H, d, 8Hz) |
| 5 | 4-Cl | H | CH₂C(CH₃)₃ | 38.3 | Oil | 3450, 3360 | 0.94(9H, s), 3.14(2H, s), 3.54(2H, bs), 4.45(2H, s), 6.4(1H, dd, 9, 3Hz), 6.76(1H, d, 3Hz), 7.0(1H, d, 9Hz) |
| 6 | 4-Cl | H | (CH₂)₅CH₃ | 47.7 | Oil | 3470, 3360, 3220 | 0.90(3H, t, 5Hz), 1.1~2.1(8H, m), 3.50(2H, t, 6Hz), 3.60(2H, s), 4.48(2H, s), 6.47(1H, dd, 8, 3Hz), 6.80(1H, d, 3Hz), 7.07(1H, d, 8Hz) |
| 7 | 4-Cl | H | (CH₂)₇CH₃ | 36.7 | Oil | 3440, 3340, 2910, 2840 | 0.84(3H, m), 1.01~1.83(12H, m), 3.43(2H, s), 3.48(2H, t, 7Hz), 4.46(2H, s), 6.43(1H, dd, 9, 3Hz), 6.76(1H, d, 3Hz), 7.03(1H, d, 9Hz) |
| 8 | 4-Cl | H | —CH₂—cyclohexyl | | | | |

TABLE 4-continued

| No. | $X^1$ | $X^2$ | R | Yield of synthesis (%) | Boiling point °C./mmHg | IR (KBr, neat, cm$^{-1}$) | NMR (CDCl$_3$, δ, ppm, 60 MHz) |
|---|---|---|---|---|---|---|---|
| 9 | 4-Cl | H | –C$_6$H$_5$ (phenyl) | 91.2 | mp 95~97 | | 3.6(2H, bs), 5.30(2H, s), 6.50(1H, dd, 8, 3Hz), 6.73~7.6(7H, m) |
| 10 | 4-Cl | | –CH$_2$–C$_6$H$_5$ | | | | |
| 11 | 4-Cl | H | CH$_2$CF$_3$ | 83.5 | 102~103/0.7 | | 3.70(2H, bs), 3.87(2H, q, 8Hz), 4.68(2H, s), 6.5~7.3(3H, m) |
| 12 | 4-Cl | H | CH$_2$CF$_2$CHF$_2$ | 61.0 | Oil | 3450, 3370 | 3.64(2H, s), 3.85(2H, tt, 13, 2Hz), 4.60(2H, s), 5.51(1H, tt, 54, 6Hz), 6.37~7.33(3H, m) |
| 13 | 4-Cl | H | CH$_2$CF$_2$CF$_3$ | 57.0 | 105–107/0.8–0.6 | 3445, 3365 | 3.57(2H, s), 3.89(2H, tt, 13, 1Hz), 4.58(2H, s), 6.41(1H, dd, 8, 3Hz), 6.55(1H, d, 3Hz), 7.00(1H, d, 8Hz) |
| 14 | 4-Cl | H | CH$_2$CF$_2$CHFCF$_3$ | 83.0 | 110~112/0.2 | 3530, 3430, 3260, 2970, 2920 | 3.60(2H, bs), 3.6~4.13(2H, m), 5.13(1H, d, 6-plet, 44, 6Hz), 4.78(2H, s), 6.50(1H, dd, 8, 3Hz), 6.70(1H, d, 3Hz), 7.10(1H, d, 8Hz) |
| 15 | 4-Cl | H | CH$_2$(CF$_2$)$_2$CF$_3$ | 92.3 | Oil | 3510, 3420, 3260, 2970, 2920 | 3.53(2H, s), 3.93(2H, tt, 14, 2Hz), 4.58(2H, s), 6.43(1H, dd, 8, 3Hz), 6.68(1H, d, 3Hz), 7.01(1H, d, 8Hz) |
| 16 | 4-Br | H | CH$_2$CF$_2$CF$_3$ | 60.0 | Oil | | 3.67(2H, s), 3.97(2H, tt, 13, 1Hz), 4.62(2H, s), 6.45(1H, dd, 8, 3Hz), 6.77(1H, d, 3Hz), 7.30(1H, d, 8Hz) |
| 17 | 4-Br | H | (CH$_2$)$_2$CH(CH$_3$)$_2$ | | | | |
| 18 | 4-I | H | CH$_2$CF$_2$CF$_3$ | 35.0 | Oil | 3440, 3360 | 3.65(2H, s), 3.93(2H, tq, 13, 2Hz), 4.51(2H, s), 6.31(1H, dd, 9, 3Hz), 6.71(1H, d, 3Hz), 7.46(1H, d, 9Hz) |
| 19 | 4-Cl | 6-Cl | CH$_2$CF$_2$CF$_3$ | 55.0 | Oil | | 4.01(2H, tt, 13, 1Hz), 4.10(2H, s), 4.67(2H, s), 6.88(1H, s), 7.30(1H, s) |
| 20 | 4-Cl | 6-Cl | (CH$_2$)$_2$CH(CH$_3$)$_2$ | 53.8 | 132/0.8 | 3480, 3360, 3200 | 0.90(6H, d, 6Hz), 1.2~2.1(3H, m), 3.50(2H, t, 6Hz), 4.01(2H, s), 4.40(2H, s), 6.83(1H, s), 7.17(1H, s) |
| 21 | 2-Cl | H | CH$_2$CF$_2$CF$_3$ | 47.0 | Oil | | 3.97(2H, tt, 13, 1Hz), 4.03(2H, s), 4.70(2H, s), 6.50~7.27(3H, m) |
| 22 | 6-Cl | H | CH$_2$CF$_2$CF$_3$ | 23.0 | 106~108/0.8 | 3465, 3375 | 3.80(2H, tt, 13, 1Hz), 4.03(2H, s), 4.43(2H, s), 6.40~7.37(3H, m) |
| 23 | 4-CH$_3$ | H | (CH$_2$)$_2$CH(CH$_3$)$_2$ | 95.0 | 108~109/0.6 mp 28.2~29.5 | 3430, 3350, 3200, 3000, 2950, 2920, 2860 | 0.90(6H, d, 6.8Hz), 1.52(2H, q, 6.8Hz), 1.74(1H, 9-plet, 6.8Hz), 2.20(3H, s), 3.51(2H, t, 6.8Hz), 4.40(2H, s), 6.55(1H, dd, 7.8, 2.4Hz), 6.73(1H, d, 2.4Hz), 6.94(1H, d, 7.8Hz), 3.6(2H, bs)* |
| 24 | 4-CH$_3$ | H | CH$_2$CF$_2$CF$_3$ | 93.0 | 82~83/0.18 | 3430, 3350, 3200, 3000, 2920, 2870 | 2.20(3H, s), 3.88(2H, tq, 13.2, 1.0Hz), 4.58(2H, s), 6.59(1H, dd, 7.8, 2.4Hz), 6.67(1H, d, 2.4Hz), 6.97(1H, d, 7.8Hz), 3.68(2H, bs)* |
| 25 | 4-Cl | H | –CH$_2$CH(CH$_3$)CH$_2$CH$_3$ | 65.2 | Oil | 3440, 3340, 3200, 2940, 2900, 2850 | 0.93(3H, d, 7Hz), 0.86(3H, t, 7Hz), 1.06~2.05(3H, m), 3.31(2H, d, 7Hz), 3.55(2H, s), 4.46(2H, s), 6.45(1H, dd, 8, 3Hz), 6.78(1H, d, 3Hz), 7.05(1H, d, 8Hz) |
| 26 | 4-Br | H | (CH$_2$)$_3$CH$_3$ | 57.0 | Oil | | 1.93(3H, t, 6Hz), 2.18~2.87(4H, m), 3.47(2H, t, 6Hz), 3.67(2H, s), |

TABLE 4-continued

| No. | X$^1$ | X$^2$ | R | Yield of synthesis (%) | Boiling point °C./mmHg | IR (KBr, neat, cm$^{-1}$) | NMR (CDCl$_3$, δ, ppm, 60 MHz) |
|---|---|---|---|---|---|---|---|
| 27 | 4-Cl | 6-F | CH$_2$CF$_2$CF$_3$ | | | | 4.40(2H, s), 6.29(1H, dd, 8, 3Hz), 6.71(1H, d, 3Hz), 7.15(1H, d, 8Hz) |
| 28 | 4-Br | H | CH$_2$CF$_3$ | | | | |
| 29 | 4-F | H | CH$_2$CF$_2$CF$_3$ | 57.0 | Oil | | 3.47(2H, s), 3.85(2H, tt, 13, 1Hz), 4.70(2H, s), 6.23~6.90(3H, m) |
| 30 | 4-CH$_3$ | H | (CH$_2$)$_3$CH$_3$ | 85.3 | 91~92/0.03 | 3430, 3350, 3210, 2955, 2930, 2860 | 0.92(3H, t, 7.3Hz), 1.40(2H, 6-plet, 7.3Hz), 1.61(2H, m), 2.20(3H, s), 3.48(2H, t, 6.4Hz), 4.40(2H, s), 6.54(1H, dd, 7.8, 2.4Hz), 6.73(1H, d, 2.4), 6.94(1H, d, 7.8Hz), 3.58(2H, bs)* |
| 31 | 4-CH$_3$ | H | CH$_2$CF$_2$CHF$_2$ | | | | |
| 32 | 4-CH$_3$ | H | CH$_2$CF$_2$CHFCF$_3$ | | | 3420, 3350, 2860, 2910 | 2.40(3H, s), 3.35(2H, s), 3.40~3.98(2H, m), 4.46(2H, s), 5.05(1H, d, 6-plet, 43, 6Hz), 6.43(1H, dd, 9, 2Hz), 6.48(1H, d, 2Hz), 6.81(1H, d, 9Hz) |
| 33 | 4-CH$_3$ | H | CH$_2$(CF$_2$)$_2$CF$_3$ | | | 3410, 3340, 2900, 2850 | 2.16(3H, s), 3.43(2H, bs), 3.85(2H, tq, 13, 3Hz), 4.51(2H, s), 6.45(1H, dd, 7, 3Hz), 6.53(1H, d, 3Hz), 6.91(1H, d, 7Hz) |
| 34 | 4-CH$_3$ | H | (CH$_2$)$_2$CH$_3$ | | | | |
| 35 | 4-CH$_3$ | H | (CH$_2$)$_5$CH$_3$ | | | | |
| 36 | 4-CH$_3$ | H | CH$_2$CF$_3$ | | | | |
| 37 | 4-Br | H | CH$_2$(CF$_2$)$_2$CF$_3$ | | | | |
| 38 | 4-CH$_2$CH$_3$ | H | CH$_2$CF$_2$CF$_3$ | 44.4 | 87~88/0.4 | 3450, 3350 | 1.17(3H, t, 8Hz), 2.56(2H, q, 8Hz), 3.60(2H, bs), 3.87(2H, tq, 14, 2Hz), 4.61(2H, s), 6.5~7.3(3H, m) |

*Measured at 250 MHz.

All of compounds of formula (II) have the selective herbicidal activities described above and are therefore widely applicable as active ingredient for a herbicidal composition used in a paddy field and a crop field.

The compounds of formula (II) can be prepared from a process according to the following Reaction Scheme. 1.

Reaction Scheme 1

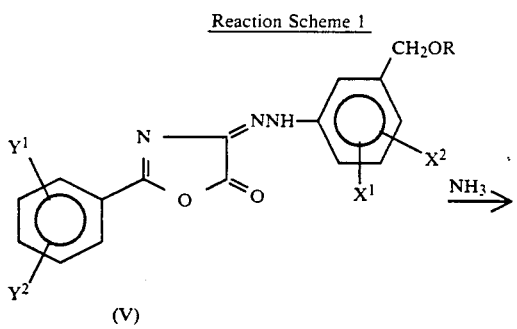

(V)

-continued
Reaction Scheme 1

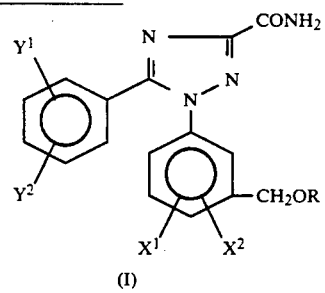

(I)

wherein R, X$^1$, X$^2$, Y$^1$ and Y$^2$ are as defined above.

A derivative of 2-phenyl-4-(phenylhydrazono)-2-oxazolin-5-one represented by the formula (V) is reacted with ammonia in an organic solvent such as acetone or toluene at a temperature of −10° to 150° C. for 0.1 to 20 hours. The resulting reaction mixture is acidified to pH 1–3 with hydrochloric acid, acetic acid or the like and then stirred at 0° to 150° C. for 0.1 to 20 hours to effect dehydration-cyclization. The process gives the compounds of formula (II) in a high yield.

The compound of formula (V) can be synthesized, for example, by a process according to the following Reaction Scheme 2.

Reaction Scheme 2

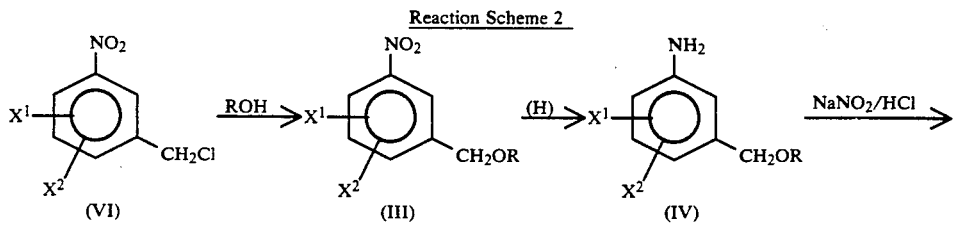

-continued
Reaction Scheme 2

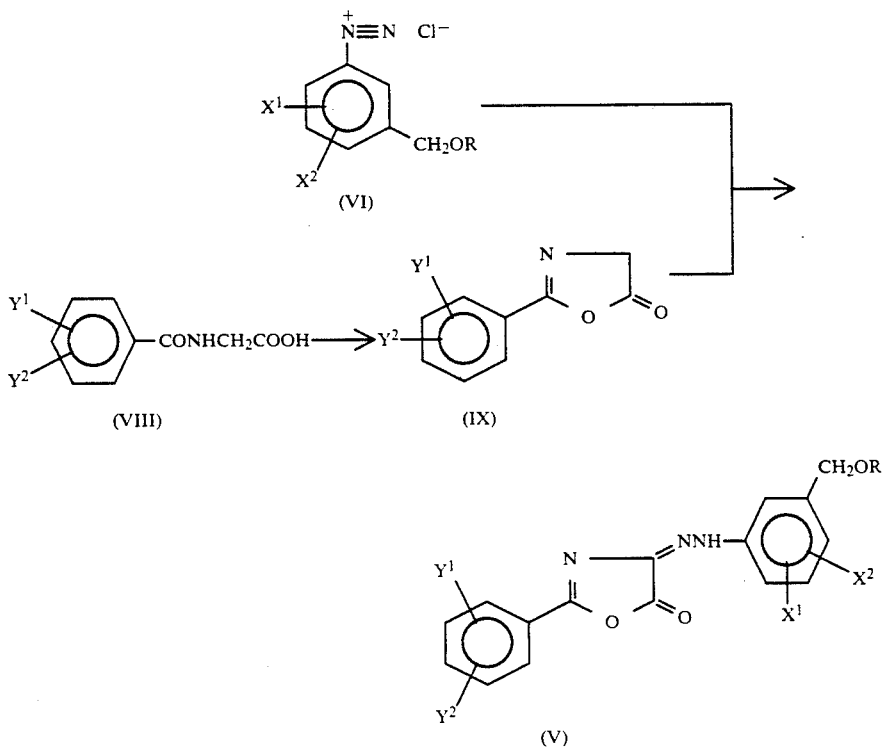

wherein R, $X^1$, $X^2$, $Y^1$ and $Y^2$ are as defined above.

A derivative of chloromethylnitrobenzene (VI) is etherified by, for example, reacting it with ROH in dimethylformamide or hexamethylphosphoramide in the presence of a hydrogen chloride acceptor such as KOH or NaH at a temperature of −10° to 150° C., preferably 0° to 80° C., for 0.1 to 20 hours, preferably 0.5 to 10 hours, to synthesize a derivative of nitrobenzyl ether (III) according to the present invention. This derivative of nitrobenzyl ether (III) is then reduced by a conventional method, for example, by adding thereto hydrazine hydrate in an alcohol solution thereof and heating the mixture under reflux in the presence of palladium-charcoal for 1 to 10 hours to obtain a derivative of aniline (IV) according to the present invention. Other reducing methods are also usable here, such as a method in which the derivative of nitrobenzyl ether (III) is reduced by using iron, zinc or tin in a solvent such as hydrochloric acid or acetic acid; a method where the derivative (III) is reduced by using colloidal sulfur or sodium sulfide in ethanol or hydrous ethanol; a method where the derivative (III) is reduced by the action of hydrazine in ethanol in the presence of ferric salt and active carbon; and a method in which the derivative (III) is catalytically reduced by hydrogen gas of ordinary pressure to 5 atom in a solvent such as ethanol or acetic acid in the presence of a catalyst such as Raney nickel, palladium carbon or platinum oxide.

Furthermore, a derivative of aniline (IV) can be prepared by catalytic reduction of a derivative of nitrobenzyl ether (III) in the presence of platinum or palladium catalyst poisoned by sulfur, morpholine or phosphorus compounds, too.

Then the derivative of aniline (IV) is converted into a diazonium salt (VII) by, for instance, using sodium nitrite in hydrochloric acid at a temperature of −10° to 15° C.

Separately, a derivative of 2-phenyl-2-oxazolin-5-one (IX) is synthesized by subjecting a derivative of hippuric acid (VIII) to dehydrating-cyclization in acetic anhydride at a temperature of 20° to 100° C., preferably 50° to 90° C., for 0.1 to 30 hours, preferably 0.1 to 3 hours. Then the diazonium salt (VII) is reacted with the derivative of 2-phenyl-2-oxazolin-5-one (IX) at a temperature of −50° to 100° C., preferably −30° to 40° C., for 0.01 to 20 hours, preferably 0.1 to 10 hours to obtain the compound represented by the formula (V).

The 1,5-diphenyl-1H-1,2,4-triazole-3-carboxamide derivatives can be used alone or in the various forms of composition such as wettable powder, emulsion, granules, powder, etc., with various types of carrier (diluent) and/or adjuvant commonly used in the preparation of agricultural chemicals.

The concentration of 1,5-diphenyl-1H-1,2,4-triazole-3-carboxamide derivative of the present invention in the compositions is preferably in the range of 0.1 to 50% by weight.

The 1,5-diphenyl-1H-1,2,4-triazole-3-carboxamide derivatives and the herbicidal composition containing such compounds as active ingredient are sprayed or spreaded on the soil of the field and/or the stalks and leaves of the plants by a known method so that the compound will be applied at a rate of preferably 0.1 to 500 g per 10 areas.

The present invention will hereinafter be described more precisely while referring the following examples, but it is to be understood that the invention is not limited by the following examples.

EXAMPLE 1 (COMPOUND 24 OF TABLE 3)

Synthesis of 3-(2,3,3,3-pentafluoropropoxy)methyl-4-methyl-1-nitrobenzene (the compound of formula (III) wherein R is $CH_2CF_2CF_3$, $X^1$ is 4—$CH_3$ and $X^2$ is H)

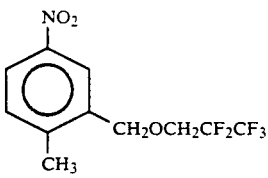

To a solution of 5.00 g (0.027 mol) of 2-methyl-5-nitrobenzyl chloride and 21.3 g (0.135 mol) of 2,2,3,3,3-pentafluoropropanol in 16.5 ml of dimethylformamide, was added 2.29 g (0.041 mol) of KOH pellets and the solution was stirred overnight. Then dichloromethane was added and the salts were filtered out. The filtrate was made acid and then the solvents were distilled off. The residue was dissolved in a 9/1 (v/v) mixed solvent of hexane/ethyl acetate, washed with dilute hydrochloric acid, water and a saturated sodium chloride aqueous solution, and then dried over magnesium sulfate. The solvents were distilled off and the resulting oil was subjected to silica gel chromatography using hexane/ethyl acetate (19/1, v/v) as developing solvent to obtain 7.71 g of 3-(2,2,3,3,3-pentafluoropropoxy)methyl-4-methyl-1-nitrobenzene having a melting point of 53.5°–54.5° C. in a 95.5% yield.

EXAMPLE 2 (COMPOUND 24 OF TABLE 4)

Synthesis of 3-(2,2,3,3,3-pentafluoropropoxy)methyl-4-methylaniline (the compound of formula (IV) in which R is $CH_2CF_2CF_3$, $X^1$ is 4—$CH_3$ and $X^2$ is H)

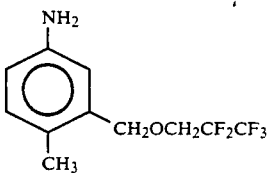

In 40 ml of ethanol, 7.30 g (0.0244 mol) of the nitro compound obtained in Example 1 was dissolved. The solution was added with 0.1 g of 10% Pd-C and 3.66 g (0.073 mol) of hydrazine hydrate and refluxed on a hot water bath for one hour. After allowed to cool by itself, the solution was passed through a Celite layer to filter out the catalyst and then washed with ethanol. The filtrate was concentrated, dissolved in dichloromethane, washed with water, a saturated sodium bicarbonate aqueous solution and a saturated sodium chloride aqueous solution, and dried over anhydrous potassium carbonate. The solvents were distilled off and the residue was fractionally distilled, collecting the fraction having a boiling point of 82°–83° C. at 0.18 mmHg. There was obtained 6.09 g of 3-(2,2,3,3,3-pentafluoropropoxy)methyl-4-methylaniline in a 93% yield.

REFERENCE EXAMPLE 1

Synthesis of 4-[[3-(2,2,3,3,3-pentafluoropropoxy)methyl-4-methylphenyl]hydrazone]-2-phenyl-2-oxazolin-5-one (the compound of formula (V) in which R is $CH_2CF_2CF_3$, $X^1$ is 4—$CH_3$ and $X^2$, $Y^1$ and $Y^2$ are all H)

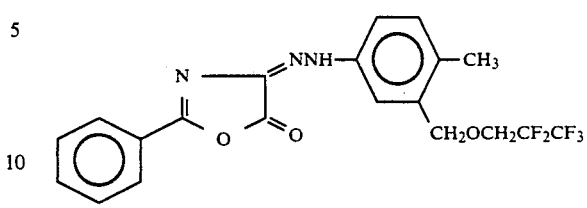

To a mixed solution of 6.9 ml of acetic acid and 1.8 ml of concentrated hydrochloric acid, was added 2.71 g (0.0101 mol) of the aniline derivative obtained in Example 2, followed by dropwise addition of a solution of 0.729 g (0.0106 mol) of sodium nitrite in 2 ml of water at a temperature below 0° C. to prepare a diazonium salt solution.

Separately, 2.08 g (0.0116 mol) of hippuric acid was added to 5.7 ml (0.0604 mol) of acetic anhydride and stirred at 80° C. for 10 minutes to obtain a solution of 2-phenyl-2-oxazolin-5-one. This solution was cooled to −20° C. and added with 1.65 g of anhydrous sodium acetate.

To this solution was added the previously prepared diazonium salt solution under stirring, and the mixed solution was further stirred at −20° to −10° C. for 2 hours and then at room temperature for 5 hours. Thereafter, water was added to the solution and the precipitated crystals were filtered out, washed well with water and dried to obtain 3.65 g (82.2% yield) of 4-[[3-(2,2,3,3,3-pentafluoropropoxy)methyl-4-methylphenyl]hydrazono]-2-phenyl-2-oxazolin-5-one. Recrystallization thereof from methylenechloride-hexane gave the orange-colored needle crystals (m.p. 160°–161° C.).

REFERENCE EXAMPLE 2

Synthesis of 1-[3-(2,2,3,3,3-pentafluoropropoxy)methyl-4-methyl]phenyl-5-phenyl-1H-1,2,4-triazole-3-carboxamide (Compound No. 28 of Table 1)

In 46 ml of acetone, 3.30 g (7.5 mmol) of 4-[[3-(2,2,3,3,3-pentafluoropropoxy)methyl-4-methylphenyl]hydrazono]-2-phenyl-2-oxazolin-5-one obtained in Reference Example 1 was suspended. To this suspension was added 1.5 ml of concentrated ammonia water, followed by one-hour stirring. The resulting solution was made acid with 1.6 ml of concentrated hydrochloric acid and further stirred at 40° to 50° C. for 30 minutes. Acetone was distilled off, and the residue was extracted with benzene. The organic layer was dried over anhydrous sodium sulfate and the solvents were distilled off to obtain a crude product. This crude product was purified by silica gel chromatography using $CH_2Cl_2$/MeOH (97/3, v/v) as developing solvent and further recrystallized to obtain 3.145 g (95.5% yield) of 1-[3-(2,2,3,3,3-pentafluoropropoxy)methyl-4-methyl]phenyl-5-phenyl-1H-1,2,4-triazole-3-carboxamide (m.p. 127°–129° C.).

REFERENCE EXAMPLE 3

Synthesis of 1-[4-methyl-3-[3-methylbutoxy)methyl]phenyl]-5-phenyl-1H-1,2,4-triazole-3-carboxamide (Compound No. 27 of Table 1)

In 40 ml of acetone, 1.668 g (4.4 mmol) of 4-[[4-methyl-3-(3-methylbutoxy)methylphenyl]hydrazono]-2-phenyl-2-oxazolin-5-one synthesized in the similar way to Examples 1~2, Reference Example 1 was suspended, followed by the addition of 1.3 ml of concentrated hydrochloric acid and one-hour stirring. The resulting solution was made acid by adding 1.5 ml of concentrated hydrochloric acid and further stirred at 40°-50° C. for 30 minutes. Acetone was distilled off and the residue was extracted with benzene. The organic layer was dried over anhydrous sodium sulfate and the solvents were distilled off to obtain a crude product. Purification of this crude product by silica gel chromatography using $CH_2Cl_2$/MeOH (97/3, v/v) as developing solvent and further recrystallization gave 1.498 g (90.0% yield) of 1-[4-methyl-3-[(3-methylbutoxy)methyl]phenyl]-5-phenyl-1H-1,2,4-triazole-3-carboxamide (m.p. 83°-85° C.)

REFERENCE EXAMPLE 4

Synthesis of 1-(3-butoxymethyl-4-chlorophenyl)-5-phenyl-1H-1,2,4-triazole-3-carboxamide (Compound No. 2 of Table 1)

In 10 ml of acetone, 1.157 g (3 mmol) of 4-[(3-butoxymethyl-4-chlorophenyl)hydrazono]-2-phenyl-2-oxazolin-5-one synthesized in the similar way to Examples 1~2, Reference Example 1 was suspended, the suspension being then added with 0.6 ml of concentrated ammonia water and stirred at room temperature for 30 minutes. The resulting solution was made acid by adding 0.6 ml of concentrated hydrochloric acid and further stirred at 50° C. for 30 minutes. Acetone was distilled off and the residue was extracted by adding benzene and water. The organic layer was washed with a saturated sodium chloride aqueous solution and dried over anhydrous sodium sulfate. The solvents were distilled off to obtain a crude product. This crude product was purified by silica gel chromatography using hexane/ethyl acetate (1/2, v/v) as developing solvent and further recrystallized to obtain 1.087 g (94.2% yield) of 1-(3-butoxymethyl-4-chlorophenyl)-5-phenyl-1H-1,2,4-triazole-3-carboxamide (m.p 96°-98° C.).

REFERENCE EXAMPLE 5

Synthesis of 1-[4-chloro-3-[(3-methylbutoxy)methyl]phenyl]-5-(2-fluorophenyl)-1H-1,2,4-triazole-3-carboxamide (Compound No. 23 of Table 1)

In 10 ml of acetone, 1.294 g (3 mmol) of 4-[4-chloro-3-[(3-methylbutoxy)methyl]phenyl hydrazono]-2-(2-fluorophenyl)-2-oxazolin-5-one synthesized in the similar way to Examples 1~2, Reference Example 1 was suspended, followed by the addition of 0.6 ml of concentrated ammonia water and 30-minute stirring at room temperature. The resulting solution was made acid by adding 0.6 ml of concentrated hydrochloric acid and further stirred at 50° C. for 30 minutes. Acetone was distilled off and the residue was extracted by adding benzene and water. The organic layer was washed with a saturated sodium chloride aqueous solution and dried over anhydrous sodium sulfate. The solvents were distilled off to obtain a crude product, and this crude product was purified by subjecting it to silica gel chromatography using hexane/ethyl acetate (1/2, v/v) as developing solvent and recrystallized from ethyl acetate-hexane to obtain 1.062 g (82.3% yield) of 1-[4-chloro-3-[(3-methylbutoxy)methyl]phenyl]-5-(2-fluorophenyl)-1H-1,2,4-triazole-3-carboxamide (m.p. 113°-115° C.).

REFERENCE EXAMPLE 6

Preparation of wettable powder

Compound No. 4 of Table 1 (50 parts), a salt of lignin sulfonic acid (5 parts), a salt of alkylsulfonic acid (3 parts) and diatomaceous earth (42 parts) are mixed and pulverized to form a wettable powder. The wettable powder is diluted with water when used.

REFERENCE EXAMPLE 7

Preparation of emulsion

Compound No. 27 of Table 1 (25 parts), xylene (65 parts) and polyoxyethylene alkylaryl ether (10 parts) are uniformly mixed to form an emulsion. The emulsion is diluted with water when used.

REFERENCE EXAMPLE 8

Preparation of granules

Compound No. 13 of Table 1 (8 parts), bentonite (40 parts), clay (45 parts) and a salt of lignin sulfonic acid (7 parts) are uniformly mixed, further kneaded by adding water, worked into granules by an extrusion granulator and dried.

In the following, the test examples on the compounds of the present invention will be given to show their selective herbicidal activities. For the sake of comparison, a herbicidal composition having as its active ingredient a compound having the following formula disclosed in Japanese Patent Application Kokai (Laid-Open) No. 98004/84 was also tested as comparative example.

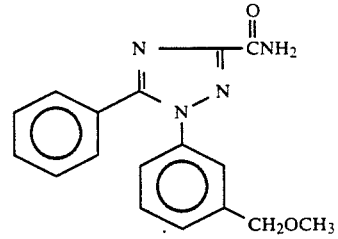

REFERENCE TEST EXAMPLE 1

Effect on crop field weeds (pre-emergence treatment)

In a planters (650×210×220 mm) having soil placed therein simulating a filed, a predetermined amount of the seeds of Amaranthus retroflexus, Bidens pilosa var. pilosa, Brassica arvensis, Stellaria media, Solanum nigrum, Abutilon theophrasti, Echinochloa crus-galli var. frumentacea, Digitaria sanguinalis, wheat and corn were sown and covered up with soil. Then the wettable powder prepared in the same manner as Reference Example 6 described above was diluted with water to a prescribed concentration and was sprayed uniformly over the soil surface by a spray gun in such an amount that the active ingredient would be applied to the soil at a rate of 200 g/10 a. Thereafter, the planters were placed and kept in a glasshouse for giving the best atmosphere for the growth of said plants.

Twenty-one days after said treatment, the herbicidal effect of each compounds on the respective weeds and the phytotoxicity to the crops by the compounds were observed and evaluated according to the following ratings. The results are shown in Table 5.

| Ratings for evaluation | |
|---|---|
| 0 | no herbicidal effect |
| 1 | not more than 30% herbicidal effect |
| 2 | 31–50% herbicidal effect |
| 3 | 51–70% herbicidal effect |
| 4 | 71–90% herbicidal effect |
| 5 | 91–100% herbicidal effect |

| Degree of phytotoxicity | | | | | |
|---|---|---|---|---|---|
| − | none | ± | slight | +++ | serious |
| + | medium | ++ | great | | | the planters. When the plants grew to the one- to two-foliage stage, the same wettable powders as used in Test Example 1 and likewise diluted with water were uniformly sprayed to the stalks and leaves of the plants and on the soil surface in the planters by a spray gun so that the active ingredient would be applied at a rate of 200 g/10 a. Then the planters were kept in the glasshouse.

Twenty-one days after said treatment, the herbicidal effect of the compositions on the weeds and phytotoxicity of the crops were observed and evaluated in the same way as in Reference Test Example 1. The results are shown in Table 6.

TABLE 5

| Compound No. of Table 1 | Amaranthus retroflexus | Bidens pilosa var. pilosa | Brassica arvensis | Stellaria media | Solanum nigrum | Abutilon theophrasti | Echinochloa crus-galli var. frumentacea | Digitaria sanguinalis | Wheat | Corn |
|---|---|---|---|---|---|---|---|---|---|---|
| 1 | 5 | 5 | 5 | 5 | 5 | 5 | 5 | 5 | — | ± |
| 2 | 5 | 5 | 5 | 5 | 5 | 5 | 5 | 5 | — | ± |
| 3 | 5 | 5 | 5 | 5 | 5 | 5 | 5 | 5 | — | ± |
| 4 | 5 | 5 | 5 | 5 | 5 | 5 | 5 | 5 | — | ± |
| 5 | 5 | 5 | 5 | 5 | 5 | 5 | 5 | 5 | — | ± |
| 6 | 5 | 5 | 5 | 5 | 5 | 5 | 5 | 5 | — | ± |
| 7 | 5 | 5 | 5 | 5 | 5 | 5 | 5 | 5 | — | ± |
| 8 | 5 | 5 | 5 | 5 | 5 | 5 | 5 | 5 | — | — |
| 9 | 4 | 5 | 5 | 5 | 4 | 3 | 5 | 5 | — | — |
| 10 | 5 | 5 | 5 | 5 | 5 | 4 | 5 | 5 | — | — |
| 11 | 5 | 5 | 5 | 5 | 5 | 5 | 5 | 5 | — | ± |
| 12 | 5 | 5 | 5 | 5 | 5 | 5 | 5 | 5 | — | ± |
| 13 | 5 | 5 | 5 | 5 | 5 | 5 | 5 | 5 | — | ± |
| 14 | 5 | 5 | 5 | 5 | 5 | 5 | 5 | 5 | — | ± |
| 15 | 5 | 5 | 5 | 5 | 5 | 5 | 5 | 5 | ± | ± |
| 16 | 5 | 5 | 5 | 5 | 5 | 5 | 5 | 5 | — | ± |
| 17 | 5 | 5 | 5 | 5 | 5 | 5 | 5 | 5 | — | ± |
| 18 | 5 | 5 | 5 | 5 | 5 | 5 | 5 | 5 | — | ± |
| 19 | 5 | 5 | 5 | 5 | 5 | 5 | 5 | 5 | — | ± |
| 20 | 5 | 5 | 5 | 5 | 5 | 4 | 4 | 5 | — | — |
| 21 | 5 | 5 | 5 | 5 | 5 | 4 | 4 | 4 | — | — |
| 22 | 5 | 5 | 5 | 5 | 5 | 5 | 4 | 3 | — | — |
| 23 | 5 | 5 | 5 | 5 | 5 | 5 | 5 | 5 | — | ± |
| 24 | 5 | 5 | 5 | 5 | 5 | 5 | 5 | 5 | — | ± |
| 25 | 5 | 5 | 5 | 5 | 5 | 5 | 5 | 5 | — | ± |
| 26 | 5 | 5 | 5 | 5 | 5 | 5 | 5 | 5 | — | ± |
| 27 | 5 | 5 | 5 | 5 | 5 | 5 | 5 | 5 | — | ± |
| 28 | 5 | 5 | 5 | 5 | 5 | 5 | 5 | 5 | — | ± |
| 29 | 5 | 5 | 5 | 5 | 5 | 5 | 5 | 5 | — | ± |
| 30 | 5 | 5 | 5 | 5 | 5 | 5 | 4 | 4 | — | — |
| 31 | 5 | 4 | 5 | 5 | 5 | 4 | 4 | 4 | — | ± |
| 32 | 5 | 5 | 5 | 5 | 5 | 5 | 5 | 5 | — | ± |
| 33 | 5 | 5 | 5 | 5 | 5 | 5 | 5 | 5 | — | ± |
| 34 | 5 | 5 | 5 | 5 | 5 | 5 | 5 | 5 | — | ± |
| 35 | 5 | 5 | 5 | 5 | 5 | 5 | 5 | 5 | — | ± |
| 36 | 5 | 5 | 5 | 5 | 5 | 4 | 4 | 5 | — | — |
| 37 | 5 | 5 | 5 | 5 | 5 | 4 | 4 | 4 | — | — |
| 38 | 5 | 5 | 5 | 5 | 5 | 5 | 4 | 5 | — | — |
| 39 | 5 | 5 | 5 | 5 | 5 | 5 | 5 | 5 | — | ± |
| 40 | 5 | 5 | 5 | 5 | 5 | 5 | 5 | 5 | — | ± |
| 41 | 5 | 5 | 5 | 5 | 5 | 5 | 5 | 5 | — | ± |
| 42 | 5 | 5 | 5 | 5 | 5 | 5 | 5 | 4 | — | ± |
| 43 | 5 | 5 | 5 | 5 | 5 | 5 | 5 | 5 | — | ± |
| 44 | 5 | 5 | 5 | 5 | 5 | 5 | 4 | 5 | — | — |
| 45 | 5 | 5 | 5 | 5 | 5 | 5 | 5 | 5 | — | — |
| 46 | 5 | 5 | 5 | 5 | 5 | 5 | 5 | 5 | — | — |
| 47 | 5 | 5 | 5 | 5 | 5 | 5 | 5 | 5 | — | ± |
| 48 | 5 | 5 | 5 | 5 | 5 | 5 | 5 | 5 | — | — |
| Comp. Example | 1 | 1 | 2 | 2 | 1 | 1 | 0 | 0 | — | — |

REFERENCE TEST EXAMPLE 2

Effect on crop field weeds (post-emergence treatment)

By following the procedures in Reference Test Example 1, the seeds of the specified plants were sown in

TABLE 5

| Compound No. of Table 1 | Amaranthus retroflexus | Bidens pilosa var. pilosa | Brassica arvensis | Stellaria media | Solanum nigrum | Abutilon theophrasti | Echinochloa crus-galli var. frumentacea | Digitaria sanguinalis | Wheat | Corn |
|---|---|---|---|---|---|---|---|---|---|---|
| 1 | 5 | 5 | 5 | 5 | 5 | 4 | 2 | 3 | — | ± |
| 2 | 5 | 5 | 5 | 5 | 5 | 5 | 2 | 4 | — | ± |
| 3 | 5 | 5 | 5 | 5 | 5 | 4 | 2 | 3 | — | ± |
| 4 | 5 | 5 | 5 | 5 | 5 | 4 | 2 | 2 | — | ± |
| 5 | 4 | 5 | 5 | 5 | 4 | 3 | 2 | 2 | — | ± |
| 6 | 5 | 5 | 5 | 5 | 5 | 5 | 2 | 5 | — | ± |
| 7 | 5 | 5 | 5 | 5 | 5 | 5 | 3 | 3 | — | ± |
| 8 | 4 | 5 | 5 | 5 | 3 | 3 | 2 | 2 | — | — |
| 9 | 4 | 5 | 5 | 5 | 4 | 3 | 2 | 2 | — | — |
| 10 | 4 | 5 | 5 | 5 | 4 | 4 | 3 | 2 | — | — |
| 11 | 5 | 5 | 5 | 5 | 5 | 5 | 2 | 2 | — | ± |
| 12 | 5 | 5 | 5 | 5 | 5 | 5 | 2 | 5 | — | + |
| 13 | 5 | 5 | 5 | 5 | 5 | 5 | 4 | 5 | — | + |
| 14 | 5 | 5 | 5 | 5 | 5 | 5 | 5 | 5 | ± | ± |
| 15 | 5 | 5 | 5 | 5 | 5 | 5 | 5 | 5 | + | ++ |
| 16 | 5 | 5 | 5 | 5 | 5 | 5 | 5 | 5 | ± | + |
| 17 | 5 | 5 | 5 | 5 | 5 | 4 | 2 | 2 | — | ± |
| 18 | 5 | 5 | 5 | 5 | 5 | 5 | 2 | 3 | — | ± |
| 19 | 5 | 5 | 5 | 5 | 5 | 3 | 2 | 3 | — | ± |
| 20 | 5 | 5 | 5 | 5 | 4 | 3 | 2 | 2 | — | — |
| 21 | 4 | 4 | 5 | 5 | 4 | 2 | 3 | 2 | — | — |
| 22 | 4 | 5 | 5 | 4 | 5 | 2 | 2 | 2 | — | — |
| 23 | 5 | 5 | 5 | 5 | 5 | 5 | 2 | 2 | — | ± |
| 24 | 5 | 5 | 5 | 5 | 5 | 5 | 5 | 5 | + | + |
| 25 | 5 | 5 | 5 | 5 | 4 | 3 | 2 | 2 | — | ± |
| 26 | 5 | 5 | 5 | 5 | 4 | 4 | 2 | 3 | — | ± |
| 27 | 5 | 5 | 5 | 5 | 5 | 4 | 4 | 3 | — | ± |
| 28 | 5 | 5 | 5 | 5 | 5 | 5 | 2 | 5 | — | ± |
| 29 | 5 | 5 | 5 | 5 | 5 | 3 | 2 | 5 | — | ± |
| 30 | 5 | 5 | 5 | 5 | 5 | 4 | 2 | 4 | — | — |
| 31 | 5 | 4 | 5 | 5 | 5 | 4 | 3 | 4 | — | ± |
| 32 | 5 | 5 | 5 | 5 | 5 | 5 | 4 | 5 | — | ± |
| 33 | 5 | 5 | 5 | 5 | 5 | 5 | 4 | 5 | — | ± |
| 34 | 5 | 5 | 5 | 5 | 5 | 4 | 2 | 4 | — | — |
| 35 | 5 | 5 | 5 | 5 | 5 | 5 | 4 | 5 | — | ± |
| 36 | 5 | 5 | 5 | 5 | 5 | 4 | 4 | 4 | — | ± |
| 37 | 4 | 5 | 5 | 5 | 4 | 4 | 2 | 2 | — | — |
| 38 | 4 | 5 | 5 | 5 | 5 | 4 | 2 | 2 | — | — |
| 39 | 5 | 5 | 5 | 5 | 5 | 5 | 3 | 3 | — | — |
| 40 | 5 | 5 | 5 | 5 | 5 | 5 | 3 | 4 | — | ± |
| 41 | 5 | 5 | 5 | 5 | 5 | 4 | 3 | 3 | — | — |
| 42 | 5 | 5 | 5 | 5 | 5 | 5 | 3 | 3 | — | — |
| 43 | 5 | 5 | 5 | 5 | 5 | 5 | 4 | 4 | — | ± |
| 44 | 5 | 5 | 5 | 5 | 5 | 4 | 2 | 3 | — | — |
| 45 | 5 | 5 | 5 | 5 | 5 | 5 | 2 | 4 | — | — |
| 46 | 5 | 5 | 5 | 5 | 5 | 5 | 4 | 5 | — | ± |
| 47 | 5 | 5 | 5 | 5 | 5 | 5 | 4 | 5 | ± | ± |
| 48 | 5 | 5 | 5 | 5 | 5 | 5 | 4 | 5 | — | ± |
| Comp. Example | 2 | 1 | 1 | 1 | 0 | 0 | 0 | 0 | — | — |

REFERENCE TEST EXAMPLE 3

Effect on paddy field weeds and phytotoxicity to rice plant

In the 1/2000-are Wagner pots packed with paddy soil and further filled with water, the seeds of *Echinochloa Crus-galli* var. *hispidula, Scirpus juncoides* subsp. *Hotauri, Alisma canaliculatum, Monochoria vaginalis* and *Cyperus difformis* were sown and the tubers of *Sagittaria pygmaea* and *Cyperus serotinus* were planted. Further, the two bifoliage seedlings of rice plant (variety: Sasanishiki) were transplanted in a pot. After keeping the pots in a hothouse for three days, the emulsions prepared in the similar way to Example 6 and diluted with water to a predetermined concentration were trickled down uniformly onto the water surface so that the active ingredient would be applied at a rate of 200 g/10 a.

Twenty-one days after said treatment, the herbicidal effect and the degree of phytotoxicity to the rice plants by the compounds were examined in the same way as in Reference Test Example 1. The results are shown in Table 7.

TABLE 7

| Compound No. of Table 1 | Echinochloa crus-galli var. hispidula | Scirpus juncoides subsp. Hotarui | Alisma canaliculatum | Monochoria vaginalis | Cyperus difformis | Sagittaria pygmaea | Cyperus serotinus | Rice plant |
|---|---|---|---|---|---|---|---|---|
| 1 | 5 | 4 | 5 | 5 | 5 | 5 | 5 | — |
| 2 | 5 | 5 | 5 | 5 | 5 | 5 | 5 | — |
| 3 | 5 | 5 | 5 | 5 | 5 | 5 | 5 | — |
| 4 | 5 | 5 | 5 | 5 | 5 | 5 | 5 | — |
| 5 | 5 | 5 | 5 | 5 | 5 | 5 | 5 | — |

TABLE 7-continued

| Compound No. of Table 1 | Echinochloa crus-galli var. hispidula | Scirpus juncoides subsp. Hotarui | Alisma canali- culatum | Monochoria vaginalis | Cyperus difformis | Sagittaria pygmaea | Cyperus serotinus | Rice plant |
|---|---|---|---|---|---|---|---|---|
| 6 | 5 | 5 | 5 | 5 | 5 | 5 | 5 | — |
| 7 | 5 | 4 | 5 | 5 | 5 | 5 | 5 | — |
| 8 | 5 | 5 | 5 | 5 | 5 | 5 | 5 | — |
| 9 | 5 | 4 | 5 | 5 | 5 | 5 | 5 | — |
| 10 | 5 | 5 | 5 | 5 | 5 | 5 | 5 | — |
| 11 | 5 | 5 | 5 | 5 | 5 | 5 | 5 | — |
| 12 | 5 | 5 | 5 | 5 | 5 | 5 | 5 | — |
| 13 | 5 | 5 | 5 | 5 | 5 | 5 | 5 | — |
| 14 | 5 | 5 | 5 | 5 | 5 | 5 | 5 | — |
| 15 | 5 | 5 | 5 | 5 | 5 | 5 | 5 | — |
| 16 | 5 | 5 | 5 | 5 | 5 | 5 | 5 | — |
| 17 | 5 | 5 | 5 | 5 | 5 | 5 | 5 | — |
| 18 | 5 | 5 | 5 | 5 | 5 | 5 | 5 | — |
| 19 | 5 | 5 | 5 | 5 | 5 | 5 | 5 | — |
| 20 | 5 | 4 | 5 | 5 | 5 | 5 | 5 | — |
| 21 | 5 | 4 | 4 | 4 | 5 | 4 | 5 | — |
| 22 | 5 | 4 | 5 | 5 | 5 | 5 | 5 | — |
| 23 | 5 | 5 | 5 | 5 | 5 | 5 | 5 | — |
| 24 | 5 | 5 | 5 | 5 | 5 | 5 | 5 | — |
| 25 | 5 | 5 | 5 | 5 | 5 | 5 | 5 | — |
| 26 | 5 | 5 | 5 | 5 | 5 | 5 | 5 | — |
| 27 | 5 | 5 | 5 | 5 | 5 | 5 | 5 | — |
| 28 | 5 | 5 | 5 | 5 | 5 | 5 | 5 | — |
| 29 | 5 | 5 | 5 | 5 | 5 | 5 | 5 | — |
| 30 | 5 | 3 | 4 | 5 | 5 | 5 | 4 | — |
| 31 | 5 | 4 | 5 | 5 | 5 | 5 | 4 | — |
| 32 | 5 | 5 | 5 | 5 | 5 | 5 | 5 | — |
| 33 | 5 | 5 | 5 | 5 | 5 | 5 | 5 | — |
| 34 | 5 | 5 | 5 | 5 | 5 | 5 | 5 | — |
| 35 | 5 | 5 | 5 | 5 | 5 | 5 | 5 | — |
| 36 | 5 | 5 | 5 | 5 | 5 | 5 | 5 | — |
| 37 | 5 | 5 | 5 | 5 | 5 | 5 | 4 | — |
| 38 | 5 | 5 | 5 | 5 | 5 | 4 | 4 | — |
| 39 | 5 | 5 | 5 | 5 | 5 | 5 | 5 | — |
| 40 | 5 | 5 | 5 | 5 | 5 | 5 | 5 | — |
| 41 | 5 | 5 | 5 | 5 | 5 | 5 | 5 | — |
| 42 | 5 | 5 | 5 | 5 | 5 | 5 | 5 | — |
| 43 | 5 | 5 | 5 | 5 | 5 | 5 | 5 | — |
| 44 | 5 | 3 | 5 | 5 | 5 | 5 | 5 | — |
| 45 | 5 | 4 | 5 | 5 | 5 | 5 | 5 | — |
| 46 | 5 | 5 | 5 | 5 | 5 | 5 | 5 | — |
| 47 | 5 | 5 | 5 | 5 | 5 | 5 | 5 | — |
| 48 | 5 | 5 | 5 | 5 | 5 | 5 | 5 | — |
| Comp. Example | 0 | 0 | 1 | 0 | 0 | 1 | 0 | — |

What is claimed is:

1. A derivative of benzyl ether represented by the formula (I):

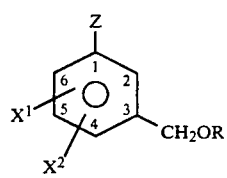

wherein R is a straight-chain alkyl group having 4 to 10 carbon atoms, a branched alkyl group having 4 to 10 carbon atoms, a cyclic alkyl group having 3 to 10 carbon atoms, an alkyl group having 1 to 3 carbon atoms which is substituted with an alicyclic structure having 3 to 7 carbon atoms, a phenyl group or an aralkyl group having 7 to 9 carbon atoms:

$X^1$ is a halogen or an alkyl group having 1 to 3 carbon atoms;

$X^2$ is a hydrogen, a halogen or an alkyl group having 1 to 3 carbon atoms; and Z is a nitro group or an amino group;

provided that when one of $X^1$ and $X^2$ is a halogen at the 4 position, the other at the 6 position is not a halogen; and further provided that when $X^1$ is an ethyl group at the 4- or the 6-position and $X^2$ is a hydrogen, R is not a phenyl group.

2. A derivative of benzyl ether represented by the formula (I):

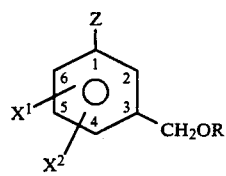

wherein R is a straight-chain alkyl group having 2 to 10 carbon atoms which is substituted with 3 to 19 fluorine atoms, or a branched alkyl group having 3 to 10 carbon atoms which is substituted with 3 to 19 fluorine atoms;

$X^1$ is a halogen or an alkyl group having 1 to 3 carbon atoms;

$X^2$ is a hydrogen, a halogen or an alkyl group having 1 to 3 carbon atoms; and Z is a nitro group or an amino group.

3. The derivative according to claim 2, wherein said derivative is 4-chloro-3-(2,2,2-trifluoroethoxy)methyl-1-nitrobenzene.

4. The derivative according to claim 2, wherein said derivative is 4-chloro-3-(2,2,3,3-tetrafluoropropoxy)methyl-1-nitrobenzene.

5. The derivative according to claim 2, wherein said derivative is 4-chloro-3-(2,2,3,3,3-pentafluoropropoxy)methyl-1-nitrobenzene.

6. The derivative according to claim 2, wherein said derivative is 4-chloro-3-(2,2,3,4,4,4-hexafluorobutoxy)methyl-1-nitrobenzene.

7. The derivative according to claim 2, wherein said derivative is 4-chloro-3-(2,2,3,3,4,4,4-heptafluorobutoxy)methyl-1-nitrobenzene.

8. The derivative according to claim 2, wherein said derivative is 3-(2,2,3,3,3-pentafluoropropoxy)methyl-4-methyl-1-nitrobenzene.

9. The derivative according to claim 2, wherein said derivative is 4-chloro-3-(2,2,2-trifluoroethoxy)methylaniline.

10. The derivative according to claim 2, wherein said derivative is 4-chloro-3-(2,2,4,4-tetrafluoropropoxy)methyl-aniline.

11. The derivative according to claim 2, wherein said derivative is 4-chloro-3-(2,2,3,3,3-pentafluoropropoxy)methyl-aniline.

12. The derivative according to claim 2, wherein said derivative is 4-chloro-3-(2,2,3,4,4,4-hexafluorobutoxy)methyl-aniline.

13. The derivative according to claim 2, wherein said derivative is 4-chloro-3-(2,2,3,3,4,4,4-heptafluorobutoxy)methyl-aniline.

14. The derivative according to claim 2, wherein said derivative is 3-(2,2,3,3,3-pentafluoropropoxy)methyl-4-methylaniline.

15. A derivative of benzyl ether represented by the formula (I):

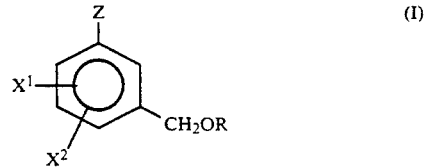

wherein R is a straight-chain alkyl group having 2 to 4 carbon atoms which is substituted with 3 to 7 fluorine atoms, $X^1$ is a chlorine or a methyl group, and $X^2$ is a hydrogen; and Z is a nitro group or an amino group.

* * * * *